US012806342B2

(12) United States Patent
Lee et al.

(10) Patent No.: US 12,806,342 B2
(45) Date of Patent: Nov. 24, 2026

(54) NEEDLELESS SYRINGE

(71) Applicant: BAZ BIOMEDIC CO., LTD., Seoul (KR)

(72) Inventors: Sung Hun Lee, Gyeonggi-do (KR); Jung Kook Kim, Daejeon (KR); Hwi Chan Ham, Seoul (KR)

(73) Assignee: BAZ BIOMEDIC CO., LTD., Seoul (KR)

( * ) Notice: Subject to any disclaimer, the term of this patent is extended or adjusted under 35 U.S.C. 154(b) by 951 days.

(21) Appl. No.: 18/287,644

(22) PCT Filed: Nov. 26, 2020

(86) PCT No.: PCT/KR2020/016909
§ 371 (c)(1),
(2) Date: Oct. 19, 2023

(87) PCT Pub. No.: WO2021/112486
PCT Pub. Date: Jun. 10, 2021

(65) Prior Publication Data

US 2024/0181162 A1 Jun. 6, 2024

(30) Foreign Application Priority Data

Dec. 5, 2019 (KR) ........................ 10-2019-0160884

(51) Int. Cl.
*A61M 5/30* (2006.01)

(52) U.S. Cl.
CPC .................................... *A61M 5/30* (2013.01)

(58) Field of Classification Search
CPC .. A61M 5/30; A61M 5/3007; A61M 5/31576; A61M 2205/106; A61D 1/025
See application file for complete search history.

(56) References Cited

U.S. PATENT DOCUMENTS 5,704,911 A 1/1998 Parsons
8,617,099 B2 12/2013 Williamson
(Continued)

FOREIGN PATENT DOCUMENTS

CN 101690834 A * 4/2010
CN 112412733 B 11/2021
(Continued)

OTHER PUBLICATIONS

CN-101690834-A Machine Translation (Year: 2009).*
(Continued)

*Primary Examiner* — Laura A Bouchelle
(74) *Attorney, Agent, or Firm* — Revolution IP, PLLC

(57) ABSTRACT

A needleless syringe, according to the present invention can cause a piston for pressurizing and injecting a drug to repeatedly reciprocate forward and backward, and thus can repeatedly inject a predetermined drug at high speed so that multiple injections, rather than a single injection, are possible during a single procedure to a wider range of skin such as that of the face in the fields of skin care and the like, wherein a user can automatically and repeatedly inject a small amount of drug at high speed without separate loading and the needleless syringe includes a recoil offset part for offsetting recoil generated during the advancing and retreating of the piston, and thus can have more improved convenience of use.

20 Claims, 14 Drawing Sheets

(56) References Cited

U.S. PATENT DOCUMENTS

| | | | |
|---|---|---|---|
| 9,629,960 | B2 | 4/2017 | Green |
| 10,806,863 | B2 | 10/2020 | Yamada et al. |
| 2004/0158195 | A1 | 8/2004 | Sibert et al. |
| 2014/0018731 | A1 | 1/2014 | Menassa |
| 2018/0056002 | A1 | 3/2018 | Shen |

FOREIGN PATENT DOCUMENTS

| | | | |
|---|---|---|---|
| EP | 3294384 | B1 | 1/2022 |
| JP | 2006-516919 | A | 7/2006 |
| JP | 4640247 | B2 | 3/2011 |
| JP | 6345978 | B2 | 6/2018 |
| KR | 10-2004-0074877 | A | 8/2004 |
| KR | 10-2014-0040125 | A | 4/2014 |
| KR | 10-1424394 | B1 | 7/2014 |
| KR | 10-1945554 | B1 | 2/2019 |
| KR | 10-2225578 | B1 | 3/2021 |
| KR | 10-2553426 | B1 | 7/2023 |
| WO | 2019-239384 | A1 | 12/2019 |

OTHER PUBLICATIONS

U.S. Appl. No. 18/287,645 (Year: 2023).*
International Search Report for PCT/KR2020/016909 mailed Mar. 15, 2021 from Korean Intellectual Property Office.

* cited by examiner

[Fig. 1]
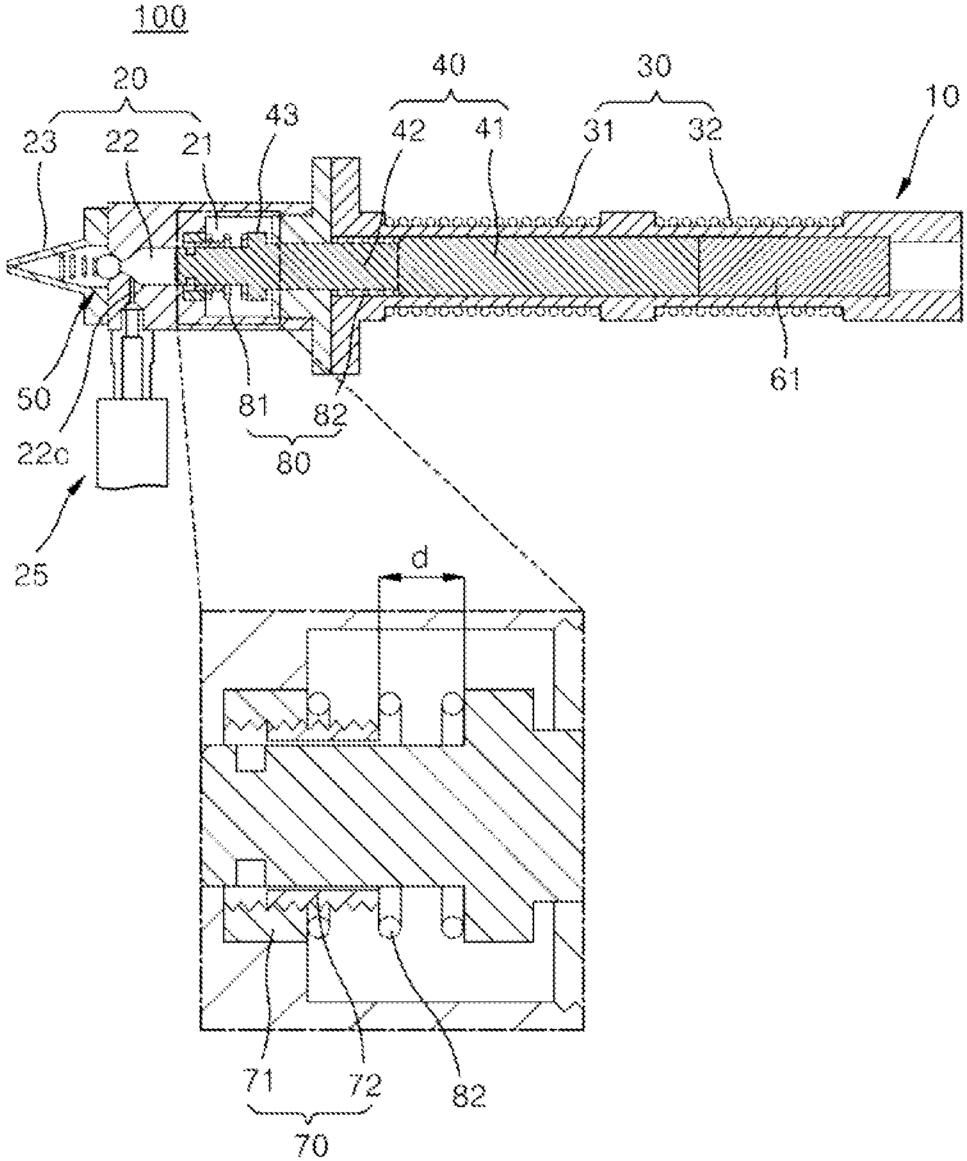

[Fig. 2]
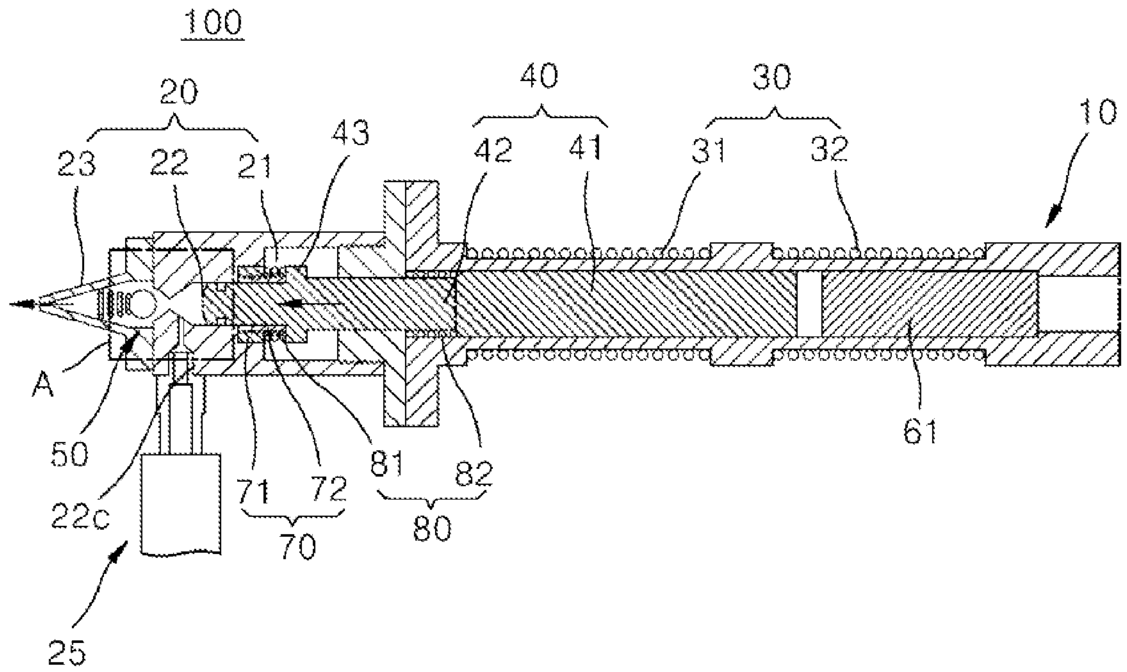
[Fig. 3]
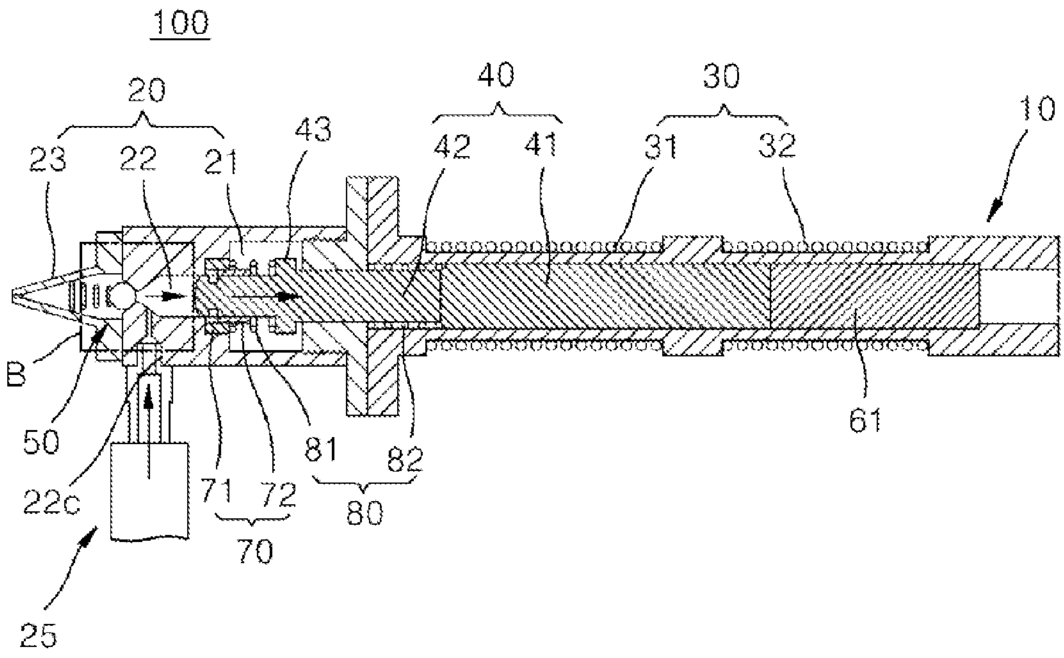

[Fig. 4]
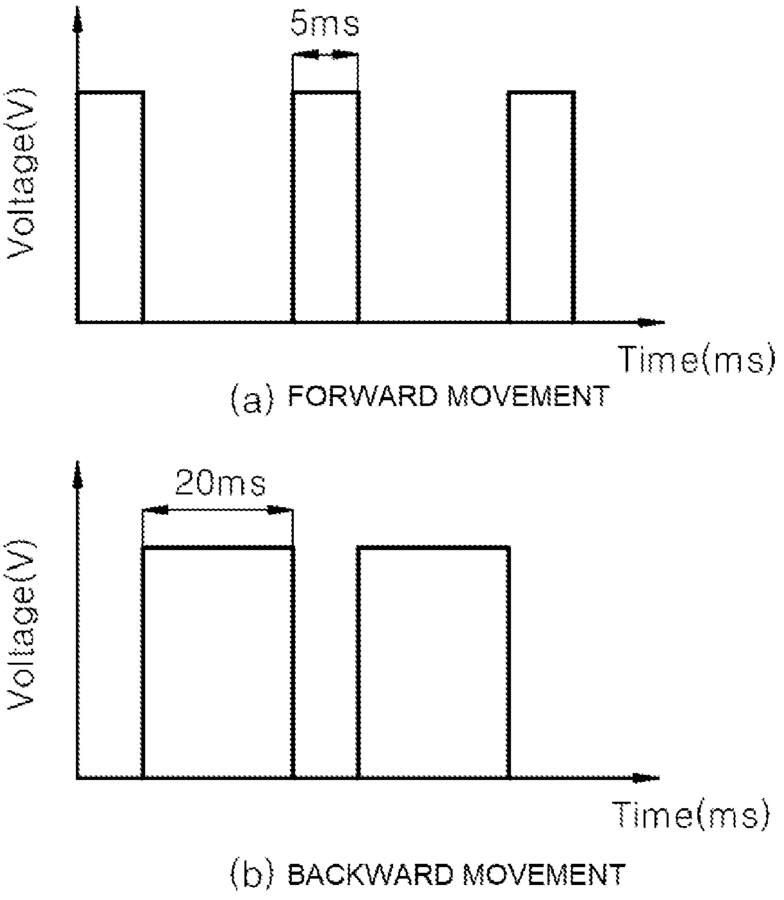

[Fig. 5]
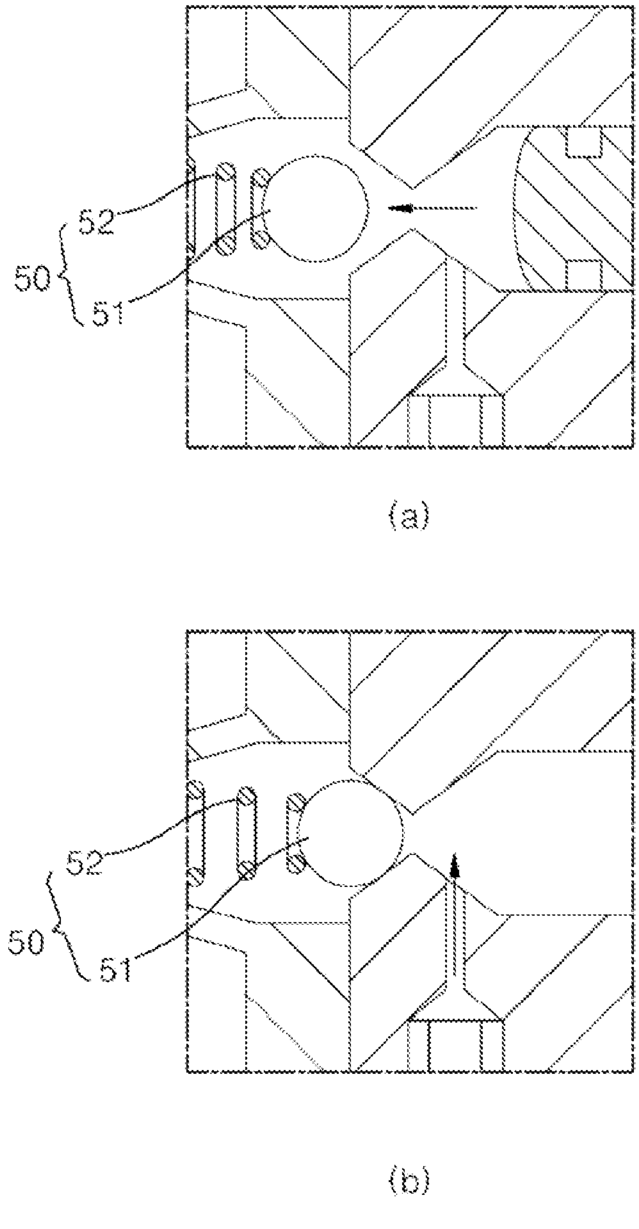

[Fig. 6]
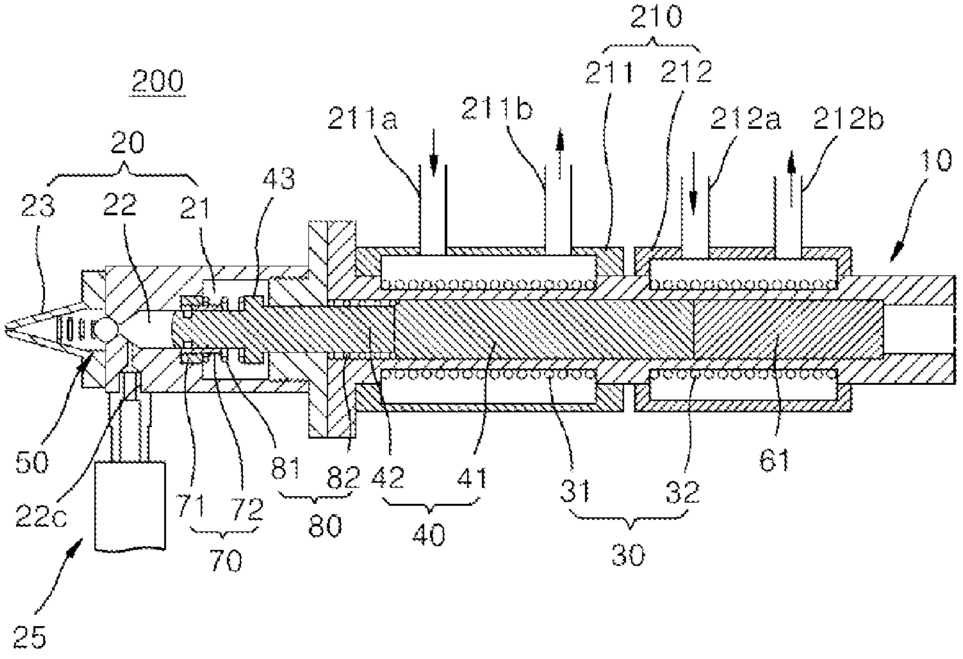

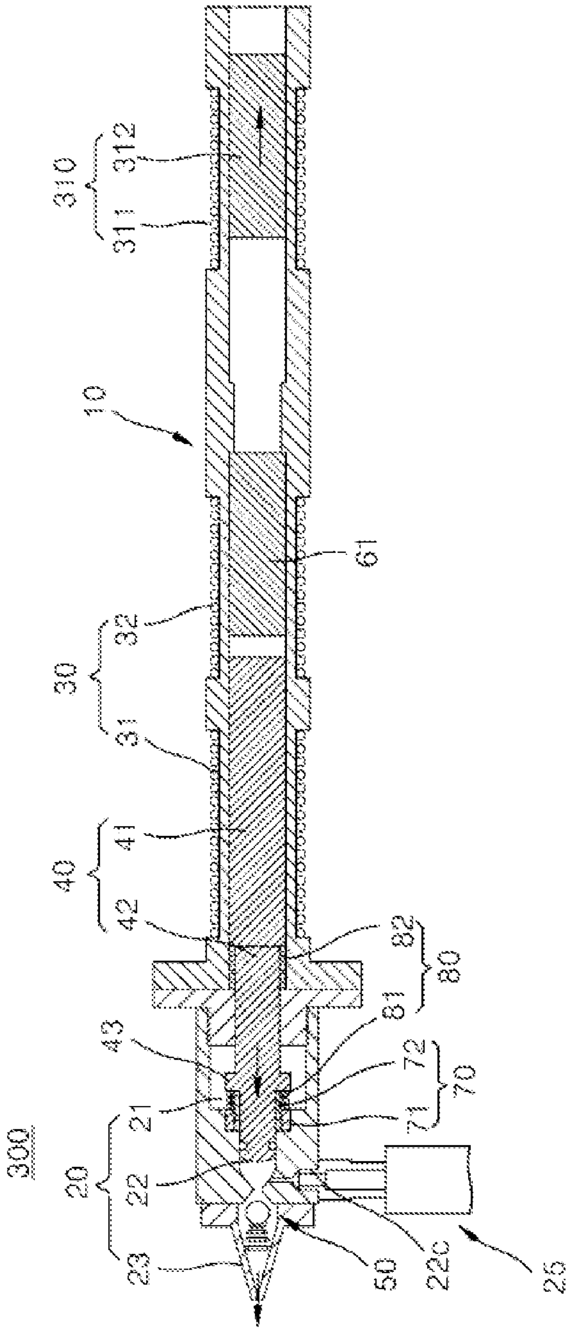
[Fig. 7]

[Fig. 8]
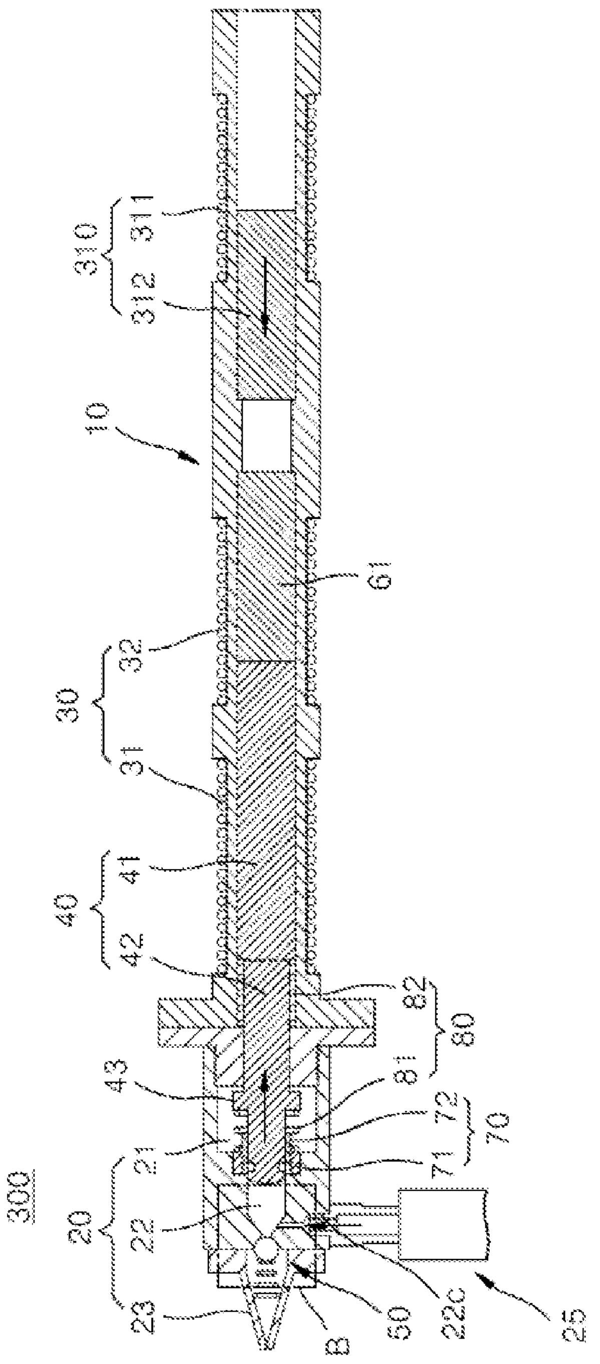

[Fig. 9]
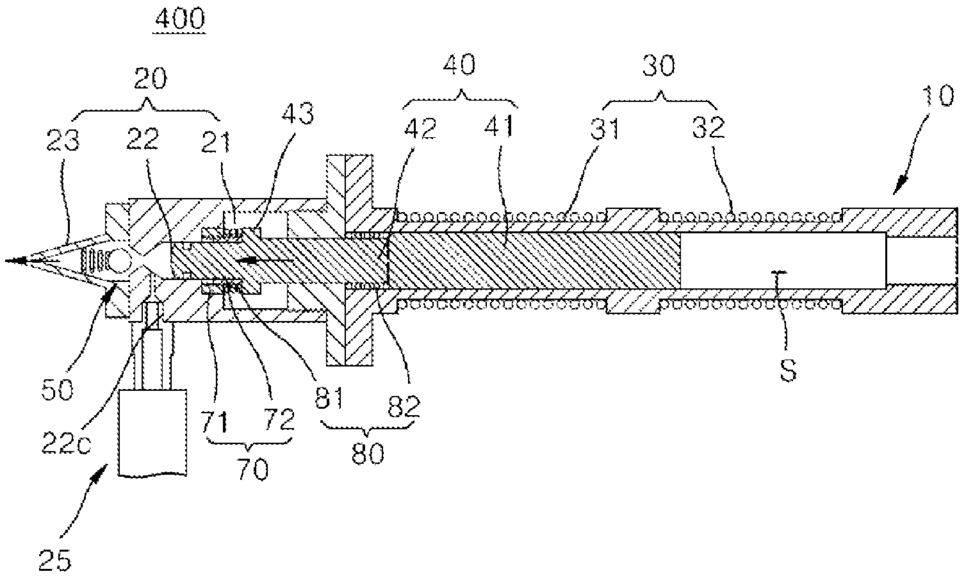
[Fig. 10]
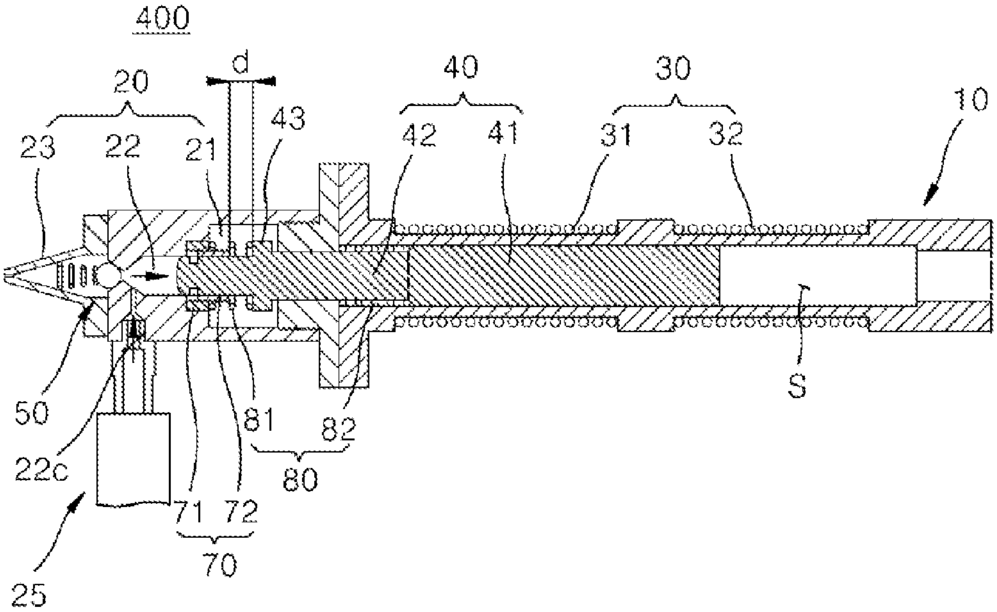

[Fig. 11]
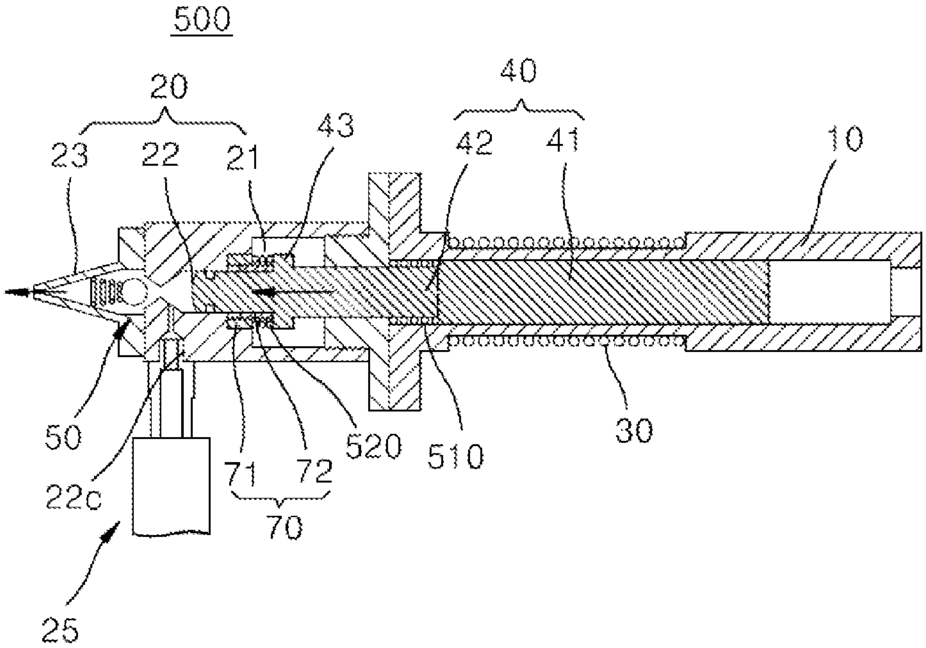
[Fig. 12]
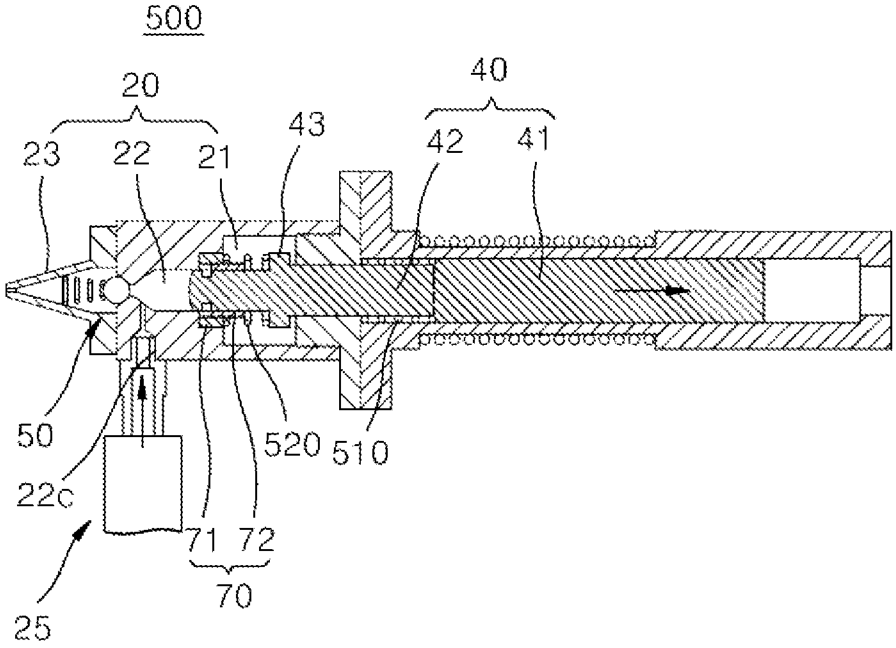

[Fig. 13]
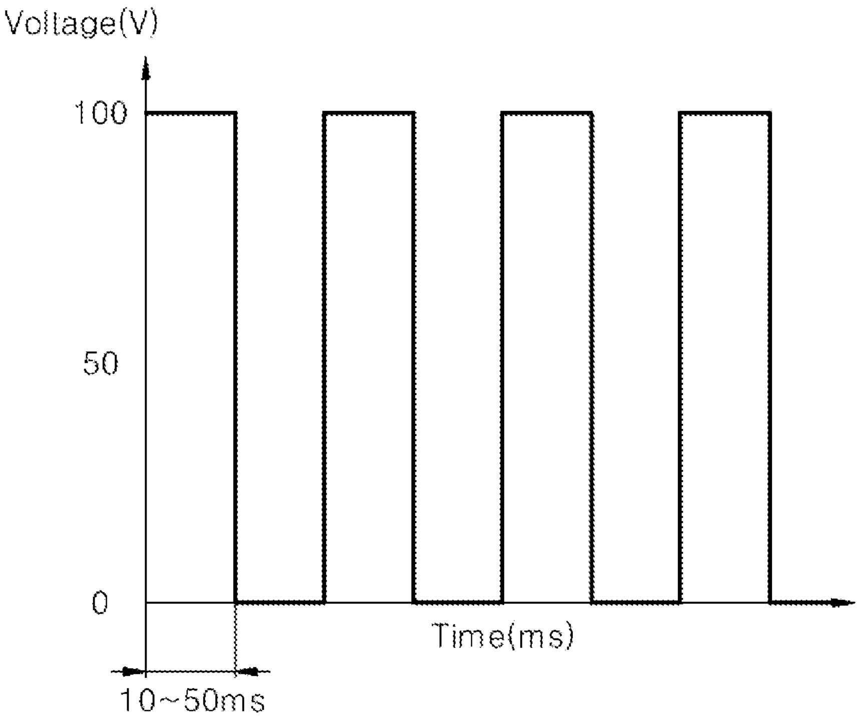
[Fig. 14]
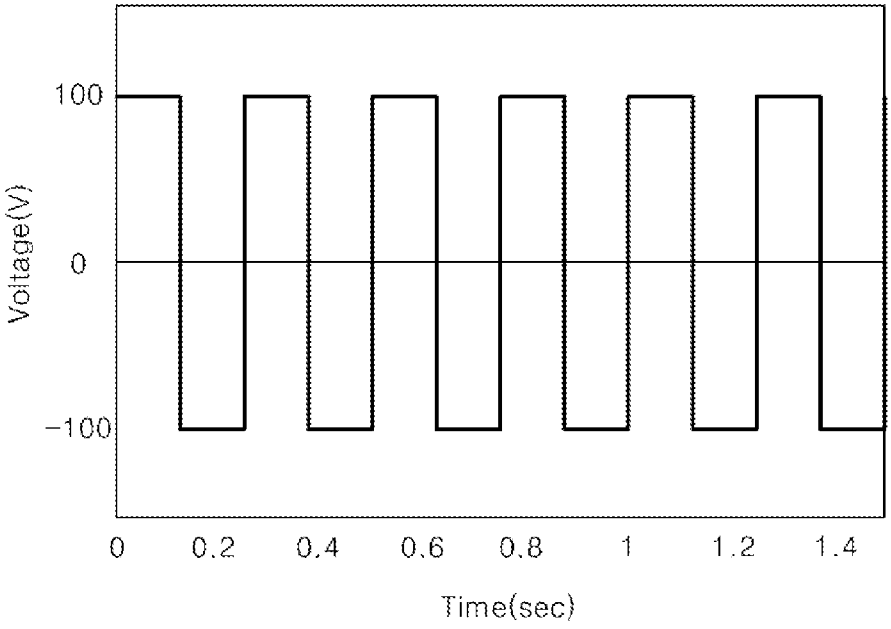

[Fig. 15]
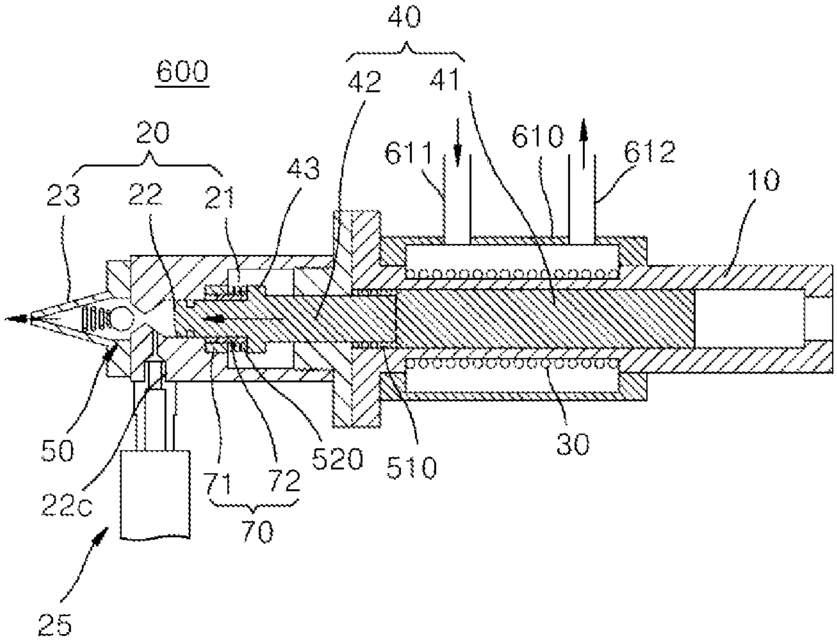

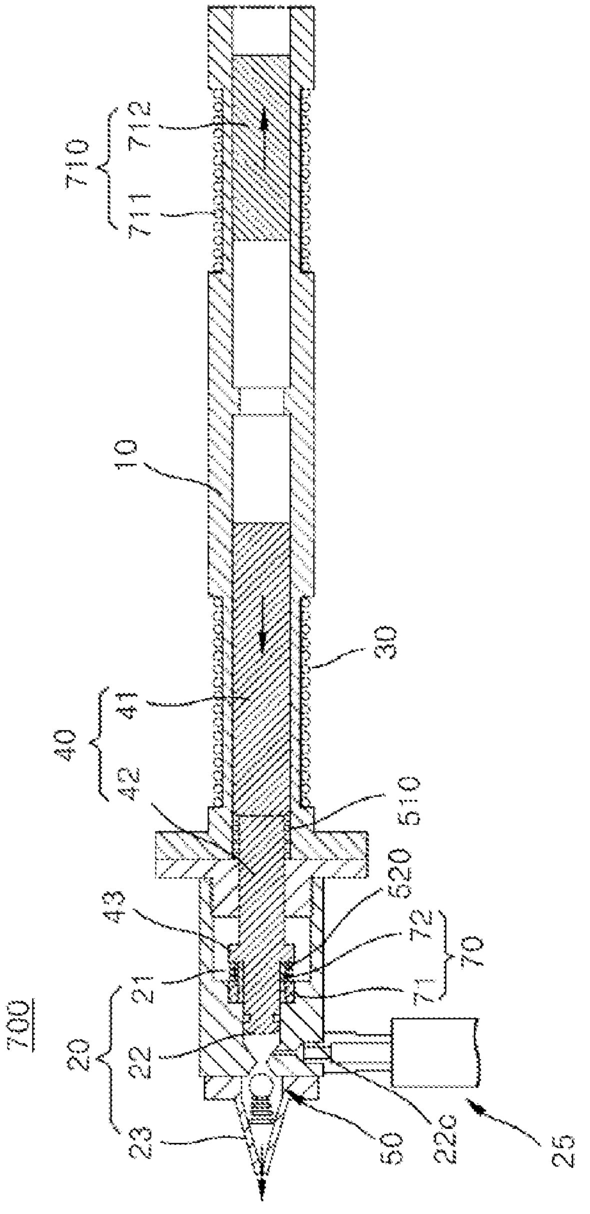
[Fig. 16]

[Fig. 17]
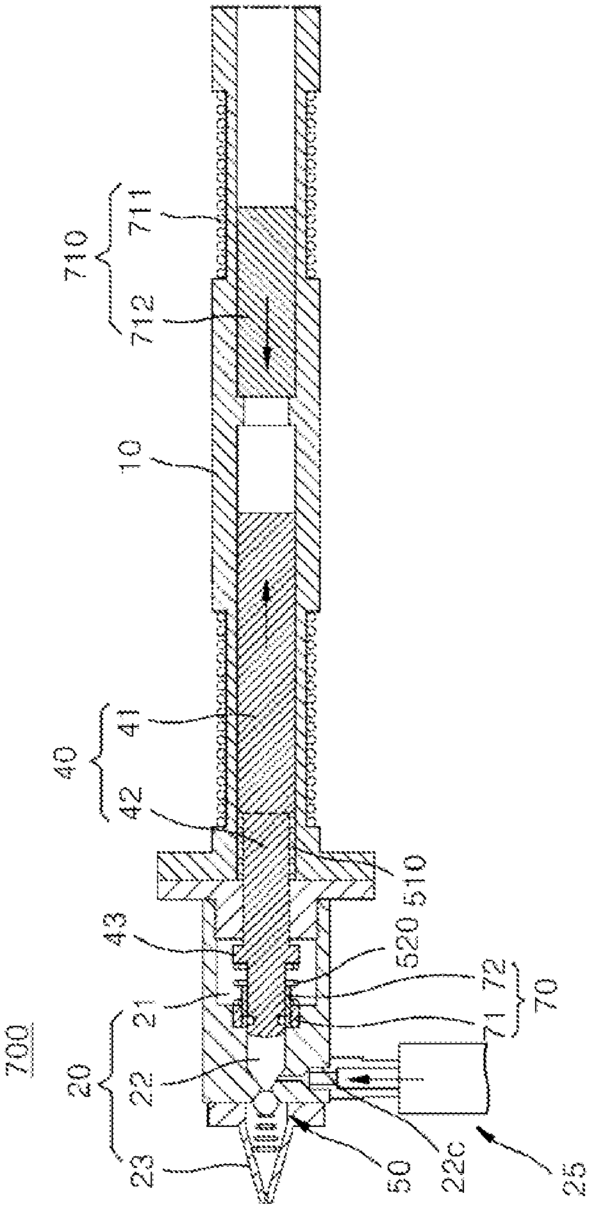

[Fig. 18]
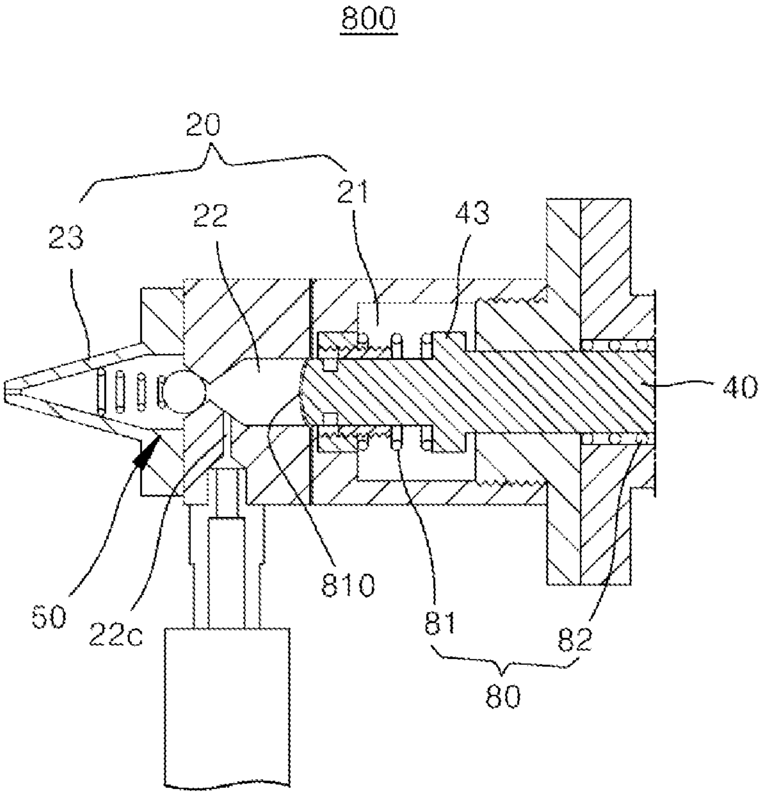

NEEDLELESS SYRINGE

CROSS REFERENCE TO PRIOR APPLICATIONS

This application is the 35 U.S.C. 371 national stage of international application PCT/KR2020/016909 filed on Nov. 26, 2020 which claims priority to Korean Patent Application No. 10-2019-0160884 filed on Dec. 5, 2019. The entire contents of each of the above-identified applications are hereby incorporated by reference.

TECHNICAL FIELD

The present invention relates to a needleless syringe, and more particularly, to a needleless syringe capable of repeatedly injecting a drug at high speed without an injection needle.

BACKGROUND ART

In general, a syringe is a device for injecting a medicinal solution into the tissue of an organism. The syringe includes a needle inserted into the body, a syringe cylinder in which the medicinal solution is accommodated, and a piston that reciprocates inside the syringe cylinder and pushes the medicinal solution with the needle. The needle is punctured to allow a drug to be injected when injected.

Recently, in order to relieve the fear of the needle of the syringe and to prevent infection due to the needle, research and development on the syringe without the needle has been actively carried out.

However, because the existing needleless syringe is configured to inject a predetermined amount of a drug into only one part of the skin at a time, damage to the skin tissue may occur.

In addition, because discomfort such as reloading after one injection follows, there is a limitation in that the needleless syringe cannot be used to evenly inject the drug multiple times into a large area of the skin in the field of skin care and the like.

DETAILED DESCRIPTION OF THE INVENTION

Technical Problem

The objective of the present invention is to provide a needleless syringe in which a small amount of a drug is repeatedly injected at high speed and is evenly injected into a larger area of the skin.

Technical Solution

According to an aspect of the present invention, there is provided a needleless syringe including: a body formed in a hollow shape; a solenoid coil wound on an outer circumferential surface of the body; a cylinder coupled to the body to be in communication with an open front surface of the body and including a drug accommodating portion in which the drug is accommodated, and a nozzle portion injecting the drug accommodated in the drug accommodating portion forward; a piston including a moving magnetic body that is long inserted into the body in a longitudinal direction and reciprocates forward and backward by a magnetic force generated when a current is applied to the solenoid coil, and a pressurizing portion that extends from the moving magnetic body, is long inserted into the cylinder in the longitudinal direction and presses the drug in the drug accommodating portion to the nozzle portion in conjunction with the forward and backward reciprocating motion of the moving magnetic body; a nozzle portion opening/closing valve that is provided to open/close a passage hole between the nozzle portion and the drug accommodating portion, is pushed by a fluidic pressure applied by the drug from the drug accommodating portion during forward movement of the piston to open the passage hole, and is elastically restored when the fluidic pressure is released to close the passage hole; and a forward/backward driving unit that repeats the supply and cut-off of current to the solenoid coil at a preset period, thereby repeating the forward movement and the backward movement of the piston, wherein the solenoid coil includes a first coil, which is wound on front of the outer circumferential surface of the body, to which a current is applied during forward movement of the piston and generates a magnetic force in a forward movement direction of the piston, and a second coil, which is wound on rear of the first coil on the outer circumferential surface of the body, to which a current is applied during backward movement of the piston and generates a magnetic force to cause the piston to move backward, and the forward/backward driving unit includes a stationary magnetic body that is inserted at a position where the stationary magnetic body is spaced apart from the moving magnetic body backward from the inside of the body and is fixed, is magnetized by a magnetic force generated when a current is applied to the second coil, and pulls the moving magnetic body in a backward movement direction due to electrical attraction, and a current supply unit that repeatedly supplies a current to the first coil and cuts off supply of current to the second coil during forward movement of the piston and repeatedly cuts off supply of current to the first coil and supplies a current to the second coil during backward movement of the piston.

The needleless syringe may further include a cooling chamber that is provided to surround an outside of the solenoid coil on an outside of the body and absorbs and cools heat generated in the solenoid coil through a cooling fluid.

The needleless syringe may further include a recoil offset part offsetting recoil generated when the piston moves forward or backward, wherein the recoil offset part includes a coil for recoil offsetting that is wound on the outer circumferential surface of the body in a position in which the coil for recoil offsetting is spaced apart from the solenoid coil backward, a moving magnetic body for recoil offsetting that is inserted into the body to be spaced apart from the piston backward by a certain distance and is provided to reciprocate forward/backward in an opposite direction to a direction of the piston due to a magnetic force generated when a current is applied to the coil for recoil offsetting, and a current supply unit for recoil offsetting that, when a current is supplied to the solenoid coil, supplies current in an opposite direction to a direction of current applied to the solenoid coil to the coil for recoil offsetting so as to generate a magnetic force in an opposite direction to a movement direction of the piston.

The needleless syringe may further include a flange portion that protrudes in a radial direction and is formed on an outer circumferential surface of the pressurizing portion and a blocker that is provided between the pressurizing portion and the cylinder and limits a forward movement distance of the piston due to the flange portion blocked when the piston moves forward, wherein the blocker includes a fixed blocker that is fixedly installed to an inner circumferential surface of the cylinder and has a female thread formed on an inner circumferential surface of the fixed blocker and formed in a ring shape, and a length adjustment blocker that is screwed to an inner circumferential surface of the fixed blocker, protrudes backward so that the flange portion is blocked by the length adjustment blocker, adjusts a coupling length at which the length adjustment blocker is coupled to the fixed blocker to adjust a length at which the length adjustment blocker protrudes backward.

The drug accommodating portion may be formed in a shape of a diverging nozzle including a reduced portion whose cross-sectional area gradually decreases toward the front, and an enlarged portion that extends from the reduced portion and increases in cross-sectional area again, and a drug supply hole for supplying the drug from the outside by a pressure difference generated when the piston moves backward, may be formed in the reduced portion.

The nozzle portion opening/closing valve may include a ball that is installed in the passage hole and an elastic member that is installed in the nozzle portion and supports the ball.

The moving magnetic body may be formed of one of a ferromagnet, a quasi-ferromagnet, and a permanent magnet, or a combination of two or more of the ferromagnet, the quasi-ferromagnet, and the permanent magnet.

The stationary magnetic body may be formed of one of a ferromagnet, a quasi-ferromagnet, and a permanent magnet, or a combination of two or more of the ferromagnet, the quasi-ferromagnet, and the permanent magnet.

The current supply unit may include a capacitor that is connected to the first coil, stores the current supplied from an external power supply source, supplies the stored current to the first coil when the piston moves forward, and cuts off supply of current to the first coil when the piston moves backward, and a direct current (DC) power supply unit that is connected to the second coil and supplies the current supplied from the external power supply source to the second coil when the piston moves backward.

The needleless syringe may further include a piston cover that is provided inside the cylinder to cover an end portion of the piston and is formed of a stretchable material so as to be stretched forward by the piston when the piston moves forward or backward.

The forward/backward driving unit may further include an elastic member that is installed between the piston and the cylinder and applies an elastic force to the piston in a backward movement direction when the piston moves backward.

According to another aspect of the present invention, there is provided a needleless syringe including: a body formed in a hollow shape; a solenoid coil wound on an outer circumferential surface of the body; a cylinder coupled to the body to be in communication with an open front surface of the body and including a drug accommodating portion in which the drug is accommodated, and a nozzle portion injecting the drug accommodated in the drug accommodating portion forward; a piston including a moving magnetic body that is long inserted into the body in a longitudinal direction and reciprocates forward and backward by a magnetic force generated when a current is applied to the solenoid coil, and a pressurizing portion that extends from the moving magnetic body, is long inserted into the cylinder in the longitudinal direction and presses the drug in the drug accommodating portion to the nozzle portion in conjunction with the forward and backward reciprocating motion of the moving magnetic body; a nozzle portion opening/closing valve that is provided to open/close a passage hole between the nozzle portion and the drug accommodating portion, is pushed by a fluidic pressure applied by the drug from the drug accommodating portion during forward movement of the piston to open the passage hole, and is elastically restored when the fluidic pressure is released to close the passage hole; and a forward/backward driving unit that repeats the supply and cut-off of current to the solenoid coil at a preset period, thereby repeating the forward movement and the backward movement of the piston, wherein the solenoid coil includes a first coil, which is wound on front of the outer circumferential surface of the body, to which a current is applied during forward movement of the piston and generates a magnetic force in a forward movement direction of the piston, and a second coil, which is wound on rear of the first coil on the outer circumferential surface of the body, to which a current is applied during backward movement of the piston and generates a magnetic force to cause the piston to move backward, and the forward/backward driving unit includes a stationary magnetic body that is inserted at a position where the stationary magnetic body is spaced apart from the moving magnetic body backward from the inside of the body and is fixed, is magnetized by a magnetic force generated when a current is applied to the second coil, and pulls the moving magnetic body in a backward movement direction due to electrical attraction, and a current supply unit that repeatedly supplies a current to the first coil and cuts off supply of current to the second coil during forward movement of the piston and repeatedly cuts off supply of current to the first coil and supplies a current to the second coil during backward movement of the piston, the needleless syringe further including a recoil offset part offsetting recoil generated when the piston moves forward or backward, a flange portion that protrudes in a radial direction and is formed on an outer circumferential surface of the piston, and a blocker that is provided between the piston and the cylinder and limits a forward movement distance of the piston due to the flange portion blocked when the piston moves forward.

According to another aspect of the present invention, there is provided a needleless syringe including: a body formed in a hollow shape; a solenoid coil wound on an outer circumferential surface of the body; a cylinder coupled to the body to be in communication with an open front surface of the body and including a drug accommodating portion in which the drug is accommodated, and a nozzle portion injecting the drug accommodated in the drug accommodating portion forward; a piston including a moving magnetic body that is long inserted into the body in a longitudinal direction and reciprocates forward and backward by a magnetic force generated when a current is applied to the solenoid coil, and a pressurizing portion that extends from the moving magnetic body, is long inserted into the cylinder in the longitudinal direction and presses the drug in the drug accommodating portion to the nozzle portion in conjunction with the forward and backward reciprocating motion of the moving magnetic body; a nozzle portion opening/closing valve that is provided to open/close a passage hole between the nozzle portion and the drug accommodating portion, is pushed by a fluidic pressure applied by the drug from the drug accommodating portion during forward movement of the piston to open the passage hole, and is elastically restored when the fluidic pressure is released to close the passage hole; and a forward/backward driving unit that repeats the supply and cut-off of current to the solenoid coil at a preset period, thereby repeating the forward movement and the backward movement of the piston.

The solenoid coil may include a first coil, which is wound on front of the outer circumferential surface of the body, to which a current is applied during forward movement of the piston and generates a magnetic force in a forward movement direction of the piston, and a second coil, which is wound on rear of the first coil on the outer circumferential surface of the body, to which a current is applied during backward movement of the piston and generates a magnetic force to cause the piston to move backward.

The forward/backward driving unit may include a current supply unit that repeatedly supplies a current to the first coil and cuts off supply of current to the second coil during forward movement of the piston and repeatedly cuts off supply of current to the first coil and supplies a current to the second coil during backward movement of the piston, and an elastic member that is installed between the piston and the cylinder and applies an elastic force to the piston in a backward movement direction when the moving magnetic body moves backward.

The forward/backward driving unit may include a current supply unit that repeatedly supplies a current to the solenoid coil and cuts off supply of current to the solenoid coil at a preset period to move the piston forward, a first elastic member that is installed between the body and the piston and applies an elastic force in a backward movement direction of the piston when supply of current of the current supply unit is cut off, and a second elastic member that is installed between the cylinder and the piston and applies an elastic force in a backward movement direction of the piston when supply of current of the current supply unit is cut off.

The forward/backward driving unit may include a current supply unit that changes a direction of current applied to the solenoid coil at a preset period repeatedly to change a direction of a magnetic force generated when a current is applied to the solenoid coil periodically, to repeat forward movement and backward movement of the piston periodically.

The current supply unit may include a capacitor that stores a current supplied from an external power supply source, supplies the stored current to the solenoid coil when the piston moves forward, and cuts off supply of current to the solenoid coil when the piston moves backward, and a direct current (DC) power supply unit that supplies a current supplied from the external power supply source to the solenoid coil when the piston moves backward.

The needleless syringe may further include a cooling chamber that is provided to surround an outside of the solenoid coil on an outside of the body and absorbs and cools heat generated in the solenoid coil through a cooling fluid.

The needleless syringe may further include a recoil offset part offsetting recoil generated when the piston moves forward or backward.

The recoil offset part may include a coil for recoil offsetting that is wound on the outer circumferential surface of the body in a position in which the coil for recoil offsetting is spaced apart from the solenoid coil backward, a moving magnetic body for recoil offsetting that is inserted into the body to be spaced apart from the piston backward by a certain distance and is provided to reciprocate forward/backward in an opposite direction to a direction of the piston due to a magnetic force generated when a current is applied to the coil for recoil offsetting, and a current supply unit for recoil offsetting that, when a current is supplied to the solenoid coil, supplies current in an opposite direction to a direction of current applied to the solenoid coil to the coil for recoil offsetting so as to generate a magnetic force in an opposite direction to a movement direction of the piston.

The needleless syringe may further include a flange portion that protrudes in a radial direction and is formed on an outer circumferential surface of the piston, and a blocker that is provided between the piston and the cylinder and limits a forward movement distance of the piston due to the flange portion blocked when the piston moves forward.

The blocker may include a fixed blocker that is fixedly installed to an inner circumferential surface of the cylinder and has a female thread formed on an inner circumferential surface of the fixed blocker and formed in a ring shape, and a length adjustment blocker, which is screwed to an inner circumferential surface of the fixed blocker, by which the flange portion is blocked and which adjusts a coupling length at which the length adjustment blocker is coupled to the fixed blocker.

The drug accommodating portion may be formed in a shape of a diverging nozzle including a reduced portion whose cross-sectional area gradually decreases toward the front, and an enlarged portion that extends from the reduced portion and increases in cross-sectional area again, and a drug supply hole for supplying the drug from the outside by a pressure difference generated when the piston moves backward, may be formed in the reduced portion.

The nozzle portion opening/closing valve may include a ball that is installed in the passage hole and an elastic member that is installed in the nozzle portion and supports the ball.

The moving magnetic body may be formed of one of a ferromagnet, a quasi-ferromagnet, and a permanent magnet, or a combination of two or more of the ferromagnet, the quasi-ferromagnet, and the permanent magnet.

The needleless syringe may further include a piston cover that is provided inside the cylinder to cover an end portion of the piston and is formed of a stretchable material so as to be stretched forward by the piston when the piston moves forward or backward.

According to another aspect of the present invention, there is provided a needleless syringe including: a body formed in a hollow shape; a solenoid coil wound on an outer circumferential surface of the body; a cylinder coupled to the body to be in communication with an open front surface of the body and including a drug accommodating portion in which the drug is accommodated, and a nozzle portion injecting the drug accommodated in the drug accommodating portion forward; a piston including a moving magnetic body that is long inserted into the body in a longitudinal direction and reciprocates forward and backward by a magnetic force generated when a current is applied to the solenoid coil, and a pressurizing portion that extends from the moving magnetic body, is long inserted into the cylinder in the longitudinal direction and presses the drug in the drug accommodating portion to the nozzle portion in conjunction with the forward and backward reciprocating motion of the moving magnetic body; a nozzle portion opening/closing valve that is provided to open/close a passage hole between the nozzle portion and the drug accommodating portion, is pushed by a fluidic pressure applied by the drug from the drug accommodating portion during forward movement of the piston to open the passage hole, and is elastically restored when the fluidic pressure is released to close the passage hole; and a forward/backward driving unit that repeats the supply and cut-off of current to the solenoid coil at a preset period, thereby repeating the forward movement and the backward movement of the piston.

The solenoid coil may include a first coil, which is wound on front of the outer circumferential surface of the body, to which a current is applied during forward movement of the piston and generates a magnetic force in a forward movement direction of the piston, and a second coil, which is wound on rear of the first coil on the outer circumferential surface of the body, to which a current is applied during backward movement of the piston and generates a magnetic force to cause the piston to move backward.

The forward/backward driving unit may include a current supply unit that repeatedly supplies a current to the first coil and cuts off supply of current to the second coil during forward movement of the piston and repeatedly cuts off supply of current to the first coil and supplies a current to the second coil during backward movement of the piston, and an elastic member that is installed between the piston and the cylinder and applies an elastic force to the piston in a backward movement direction when the moving magnetic body moves backward.

The forward/backward driving unit may include a current supply unit that repeatedly supplies a current to the solenoid coil and cuts off supply of current to the solenoid coil at a preset period to move the piston forward, a first elastic member that is installed between the body and the piston and applies an elastic force in a backward movement direction of the piston when supply of current of the current supply unit is cut off, and a second elastic member that is installed between the cylinder and the piston and applies an elastic force in a backward movement direction of the piston when supply of current of the current supply unit is cut off.

The forward/backward driving unit may include a current supply unit that changes a direction of current applied to the solenoid coil at a preset period repeatedly to change a direction of a magnetic force generated when a current is applied to the solenoid coil periodically, to repeat forward movement and backward movement of the piston periodically.

The current supply unit may include a capacitor that stores a current supplied from an external power supply source, supplies the stored current to the solenoid coil when the piston moves forward, and cuts off supply of power to the solenoid coil when the piston moves backward, and a direct current (DC) power supply unit that supplies a current supplied from the external power supply source to the solenoid coil when the piston moves backward.

The needleless syringe may further include a cooling chamber that is provided to surround an outside of the solenoid coil on an outside of the body and absorbs and cools heat generated in the solenoid coil through a cooling fluid.

The needleless syringe may further include a recoil offset part offsetting recoil generated when the piston moves forward or backward, wherein the recoil offset part includes a coil for recoil offsetting that is wound on the outer circumferential surface of the body in a position in which the coil for recoil offsetting is spaced apart from the solenoid coil backward, a moving magnetic body for recoil offsetting that is inserted into the body to be spaced apart from the piston backward by a certain distance and is provided to reciprocate forward/backward in an opposite direction to a direction of the piston due to a magnetic force generated when a current is applied to the coil for recoil offsetting, and a current supply unit for recoil offsetting that, when a current is supplied to the solenoid coil, supplies current in an opposite direction to a direction of current applied to the solenoid coil to the coil for recoil offsetting so as to generate a magnetic force in an opposite direction to a movement direction of the piston.

Effects of the Invention

A needleless syringe according to the present invention is configured to cause a piston for pressurizing and injecting a drug to repeatedly reciprocate forward and backward, and thus can repeatedly inject a predetermined drug at high speed so that multiple injections, rather than a single injection, are possible during a single procedure to a wider range of skin such as that of the face in the fields of skin care and the like.

In addition, a user can automatically and repeatedly inject a small amount of drug at high speed without separate loading.

Furthermore, the needleless syringe according to the present invention includes a recoil offset part for offsetting recoil generated during the advancing and retreating of the piston, and thus can have more improved convenience of use.

Furthermore, voltage applied to a solenoid coil and the coupling length of a length adjustment blocker are changed so that one injection amount of the drug can be adjusted.

Moreover, a piston cover is provided between a cylinder and the piston so as to prevent the drug from staining the end portion of the piston, and thus the user does not have to wipe the end portion of the piston.

DESCRIPTION OF THE DRAWINGS

FIG. 1 is a cut perspective view showing a needleless syringe according to a first embodiment of the present invention.

FIG. 2 is a view showing a forward movement state of a piston of the needleless syringe according to the first embodiment of the present invention.

FIG. 3 is a view showing a backward movement state of the piston of the needleless syringe according to the first embodiment of the present invention.

FIG. 4 is a graph showing a current supply waveform applied to a solenoid coil of the needleless syringe according to the first embodiment of the present invention.

FIG. 5 is a view showing a nozzle opening/closing valve of the needleless syringe according to the first embodiment of the present invention.

FIG. 6 is a cross-sectional view showing a needleless syringe according to a second embodiment of the present invention.

FIG. 7 is a view showing a forward movement state of a piston of a needleless syringe according to a third embodiment of the present invention.

FIG. 8 is a view showing a backward movement state of the piston of the needleless syringe according to the third embodiment of the present invention.

FIG. 9 is a view showing a forward movement state of a piston of a needleless syringe according to a fourth embodiment of the present invention.

FIG. 10 is a view showing a backward movement state of the piston of the needleless syringe according to the fourth embodiment of the present invention.

FIG. 11 is a view showing a forward movement state of a piston of a needleless syringe according to a fifth embodiment of the present invention.

FIG. 12 is a view showing a backward movement state of the piston of the needleless syringe according to the fifth embodiment of the present invention.

FIG. 13 is a graph showing an example of a current supply waveform applied to a solenoid coil of the needleless syringe according to the fifth embodiment of the present invention.

FIG. 14 is a graph showing another example of a current supply waveform applied to the solenoid coil of the needleless syringe according to the fifth embodiment of the present invention.

FIG. 15 is a cross-sectional view showing a needleless syringe according to a sixth embodiment of the present invention.

FIG. 16 is a view showing a forward movement state of a piston of a needleless syringe according to a seventh embodiment of the present invention.

FIG. 17 is a view showing a backward movement state of the piston of the needleless syringe according to the seventh embodiment of the present invention.

FIG. 18 is a cross-sectional view showing a needleless syringe according to an eighth embodiment of the present invention.

MODE OF THE INVENTION

Hereinafter, embodiments of the present invention will be described with reference to the accompanying drawings.

FIG. 1 is a cut perspective view showing a needleless syringe according to a first embodiment of the present invention.

Referring to FIG. 1, a needleless syringe 100 according to the first embodiment of the present invention includes a body 10, a cylinder 20, a solenoid coil 30, a piston 40, a nozzle portion opening/closing valve 50, a forward/backward driving unit, a blocker 70, and an elastic member 80.

The body 10 is formed in a hollow shape and is formed to be elongated in a longitudinal direction. The front surface of the body 10 is formed to be opened.

The cylinder 20 is screwed to the front of the body 10. The cylinder 20 is coupled to the body 10 to be in communication with the open front surface of the body 10.

The cylinder 20 is formed in a hollow shape and is formed in such a way that a cylinder main hole 21, a drug accommodating portion 22 and a nozzle portion 23 are in communication with each other.

The cylinder main hole 21 is formed in the rear of an inner side of the cylinder 20, and a thread is formed in such a way that the front end of the body 10 is inserted into at least a part of the cylinder 20 to be screw-coupled to each other.

The drug accommodating portion 22 is formed to have a reduced cross-sectional area compared to a body coupling hole 21. The drug accommodating portion 22 is a passage through which the piston 40 is in close contact with the drug accommodating portion 22, and is an accommodation space in which a drug is accommodated.

The drug accommodating portion 22 is formed in a shape of a diverging nozzle including a reduced portion **22*a* whose cross-sectional area gradually decreases toward the front, and an enlarged portion 22*b* that extends from the reduced portion 22*a* and increases in cross-sectional area again. A drug supply hole 22*c* for supplying the drug from the outside by a pressure difference generated when the piston 40 moves backward is formed in the reduced portion 22*a*. A drug filling device 25 is coupled to the drug supply hole 22*c***.

The nozzle portion 23 is formed to be in communication with the drug accommodating portion 22 and to have a gradually decreasing cross-sectional area, and injects the drug accommodated in the drug accommodating portion 22.

In the present embodiment, an example in which the cylinder 20 is formed by coupling a first block in which the body coupling hole 21 and the drug accommodating portion 22 are formed and a second block in which the nozzle portion 23 is formed, will be described. However, the present invention is not limited thereto, and the first block and the second block may also be integrally formed.

The solenoid coil 30 is wound on an outer circumferential surface of the body 10 and generates a magnetic force when a current is applied to the solenoid coil 30.

The solenoid coil 30 includes a first coil 31 and a second coil 32. The first coil 31 and the second coil 32 are disposed to be spaced apart from each other by a certain distance in a longitudinal direction of the body 10.

The first coil 31 is a coil, which is wound on the front of the outer circumferential surface of the body 10 and to which a current is applied when the piston 40 moves forward. The first coil 31 generates a magnetic force in a direction in which the piston 40 moves forward when a current is applied, so as to move the piston 40 forward.

The second coil 32 is a coil, which is wound on the rear of the outer circumferential surface of the body 10 and to which a current is applied when the piston 40 moves backward. The second coil 32 causes the piston 40 to move backward when a current is applied.

The piston 40 is long inserted into the body 10 and the cylinder 20 in the longitudinal direction and pushes the drug accommodated in the drug accommodating portion 22.

In the piston 40, a moving magnetic body 41 and a pressurizing portion 42 are integrally formed.

The moving magnetic body 41 is long inserted into the body 10 in the longitudinal direction, and reciprocates forward and backward by a magnetic force generated when a current is applied to the first coil 31. The moving magnetic body 41 may be formed of one of a ferromagnet, a quasi-ferromagnet, and a permanent magnet, or a combination of two or more of the ferromagnet, the quasi-ferromagnet, and the permanent magnet.

The pressurizing portion 42 extends from the moving magnetic body 41 forward and is long inserted into the cylinder 20 in the longitudinal direction. The pressurizing portion 42 presses the drug in the drug accommodating portion 22 to the nozzle portion 23 in conjunction with the forward and backward reciprocating motion of the moving magnetic body 41. The pressurizing portion 42 may be formed of the same material as a material for forming the moving magnetic body 41 and may also be formed of a different material from the material for forming the moving magnetic body 41 and then may be integrally combined with the moving magnetic body 41.

A flange portion 43 protruding in a radial direction is formed on the outer circumferential surface of the pressurizing portion 42 to limit a moving distance of the piston 40.

The flange portion 43 is blocked by a length adjustment blocker 72 to be described later during the forward movement of the piston 40 so that a forward movement distance of the piston 40 is limited.

The blocker 70 is detachably coupled between the cylinder 20 and the piston 40.

The blocker 70 includes a fixed blocker 71 coupled to and fixed to the cylinder main hole 21, and a length adjustment blocker 72 that is screwed to an inner circumferential surface of the fixed blocker 71 and adjusts a length at which the length adjustment blocker 72 is coupled to the fixed blocker 71.

The fixed blocker 71 has a female thread formed on an inner circumferential surface of the fixed blocker 71 and formed in a ring shape.

The length adjustment blocker 72 has a male thread on an outer circumferential surface of the length adjustment blocker 72 and formed in a ring shape. A predetermined interval is formed between the length adjustment blocker 72 and the piston 40, and the pressurizing portion 42 of the piston 40 may pass through the inside of the length adjustment blocker 72 to move forward and backward.

The length adjustment blocker 72 is screwed at the rear of the fixed blocker 72, and a coupling length at which the length adjustment blocker 72 is screw-coupled to the fixed blocker 72, may be adjusted differently depending on one injection amount of the drug.

As the length of the length adjustment blocker 72 screwed to the fixed blocker 71 increases, the length at which the length adjustment blocker 72 protrudes backward decreases. When the length of the length adjustment blocker 72 protruding backward decreases, a distance d between the length adjustment blocker 72 and the flange portion 43 increases, so that a forward movement distance d of the piston 40 increases. As the forward movement distance d of the piston 40 increases, one injection amount of the drug is increased.

As the coupling length at which the length adjustment blocker 72 is screwed to the fixed blocker 71 decreases, the length at which the length adjustment blocker 72 protrudes backward increases. As the length at which the length adjustment blocker 72 protruding backward increases, the distance d between the length adjustment blocker 72 and the flange portion 43 decreases, so that the forward movement distance d of the piston 40 decreases. As the forward movement distance d of the piston decreases, one injection amount of the drug is reduced.

Thus, the user may finely adjust one injection amount of the drug by adjusting the length at which the length adjustment blocker 72 is coupled to the fixed blocker 71.

The elastic member 80 includes a first elastic member 81 installed between the body 10 and the moving magnetic body 41 of the piston 40, and a second elastic member 82 installed between the cylinder 20 and the pressurizing portion 42 of the piston 40.

The first elastic member 81 is a spring that is compressed when the moving magnetic body 41 moves forward by a current supplied to the first coil 31 and applies an elastic force to the moving magnetic body 41 in the backward movement direction of the moving magnetic body 41 when the supply of current to the first coil 31 is cut off.

The second elastic member 82 is a spring that is compressed when the pressurizing portion 42 moves forward by a current supplied to the first coil 31 and applies an elastic force to the pressurizing portion 42 in the backward movement direction of the pressurizing portion 42 when the supply of current to the first coil 31 is cut off.

The nozzle portion opening/closing valve 50 is provided to open and close a passage hole between the nozzle portion 23 and the drug accommodating portion 22. The nozzle portion opening/closing valve 50 is pushed by a fluidic pressure applied by the drug accommodated in the drug accommodating portion 22 during the forward movement of the piston 40 to open the passage hole, and is elastically restored when the fluidic pressure is released to close the passage hole.

The nozzle portion opening/closing valve 50 includes a ball 51 installed in the passage hole, and an elastic member 52 that is installed in the nozzle portion 23 to provide an elastic force in a direction of the ball 51 toward the drug accommodating portion 22. The ball 51 is formed to fit into the enlarged portion **22*b*. In the present embodiment, the nozzle portion opening/closing valve 50 has been described as an example of a ball valve. However, the present invention is not limited thereto, and various valves such as a duckbill valve, a plate check valve, an electric control valve, and the like may be used as the nozzle portion opening/closing valve 50**.

The forward/backward driving unit may repeat the supply and cut-off of current to the first coil 31 and the second coil 32 at a preset period, thereby repeating the forward movement and the backward movement of the piston 40 a plurality of times.

The forward/backward driving unit includes a stationary magnetic body 61 and a current supply unit (not shown).

The stationary magnetic body 61 is inserted at a position where the stationary magnetic body 61 is spaced apart from the moving magnetic body 41 backward from the inside of the body 10 and is fixed. The stationary magnetic body 61 is magnetized by a magnetic force generated when a current is applied to the second coil 32, and is polarized. When the stationary magnetic body 61 is polarized, the stationary magnetic body 61 pulls the moving magnetic body 41 in a backward movement direction due to electrical attraction. The stationary magnetic body 61 may be formed of one of a ferromagnet, a quasi-ferromagnet, and a permanent magnet, or a combination of two or more of the ferromagnet, the quasi-ferromagnet, and the permanent magnet.

The current supply unit (not shown) applies a current only to the first coil 31 and cuts off the current to the second coil 32 when the piston 40 moves forward, and cuts off the current to the first coil 31 and applies a current to the second coil 32 when the piston 40 moves backward.

The current supply unit (not shown) include a capacitor (not shown) that is connected to the first coil 31 and stores the current supplied from an external power supply source, and a direct current (DC) power supply unit (not shown) that is connected to the second coil 32 and supplies the current supplied from the external power supply source to the second coil.

The capacitor (not shown) supplies the stored current to the first coil 31 when the piston 40 moves forward and discharges, and when the piston 40 moves backward, the capacitor (not shown) stores the current and charges without supplying a current to the first coil 31. Thus, because an electric energy applied during the forward movement of the piston 40 is greater than the electric energy applied during the backward movement, forward movement speed may be increased.

The operation of the needleless syringe 100 according to the first embodiment of the present invention configured as described above will be described as follows.

FIG. 2 is a view showing a forward movement state of the piston of the needleless syringe according to the first embodiment of the present invention.

Referring to FIG. 2, first, the forward/backward driving unit applies a current to the first coil 31 and cuts off the supply of current to the second coil 32.

In this case, the current stored in the capacitor (not shown) is supplied to the first coil 31.

When a current is supplied to the first coil 31, a magnetic force between the first coil 31 and the moving magnetic body 41 is generated. The magnetic force may be adjusted according to a voltage applied to the first coil 31. One injection amount of the drug can be adjusted by changing the magnetic force.

The moving magnetic body 41 has a polarity, and the piston 40 moves forward by the magnetic force generated by the first coil 31.

When the piston 40 moves forward, the second elastic member 82 is compressed.

The piston 40 may only move forward until the flange portion 43 is blocked by the length adjustment block 72.

When the piston 40 moves forward, the pressurizing portion 42 pressurizes the drug in the drug accommodating portion 22.

Referring to FIG. 5A, when the drug in the drug accommodating portion 22 is pressurized, the nozzle portion opening/closing valve 50 is opened by the fluidic pressure.

When the nozzle portion opening/closing valve 50 is opened, the drug in the drug accommodating portion 22 may be injected forward through the nozzle portion 23.

When the piston 40 moves forward, as described above, because the piston 40 may only move forward until the flange portion 43 is blocked by the length adjustment blocker 72, the forward movement distance of the piston 40 is limited.

Thus, the coupling length at which the length adjustment blocker 72 is coupled to the fixed blocker 71, is adjusted to adjust the length at which the length adjustment blocker 72 protruding backward toward the flange portion 43 so that the forward movement distance of the piston 40 can be adjusted. By adjusting the forward movement distance of the piston 40, one injection amount of the drug may be adjusted.

That is, one injection amount of the drug is adjustable according to the magnitude of the voltage applied to the first coil 31 and the forward movement distance of the piston 40.

Meanwhile, the current supply unit supplies a current to the first coil 31 for a first preset time, and then, when the first preset time elapses, the supply of current to the first coil 31 is cut off.

Referring to FIG. 4A, a case where the first preset time is about 5 ms, will be described.

When the first preset time elapses, the forward/backward movement driving unit cuts off the supply of current to the first coil 31, and supplies a current to the second coil 32, thereby moving the piston 40 backward.

FIG. 3 is a view showing a backward movement state of the piston of the needleless syringe according to the first embodiment of the present invention.

Referring to FIG. 3, when a current is supplied to the second coil 31, a magnetic force between the second coil 32 and the stationary magnetic body 61 is generated.

The stationary magnetic body 61 has a polarity by the magnetic force and is magnetize.

In addition, when the supply of current to the first coil 31 is cut off, the magnetic force by the first coil 31 disappears and thus, the moving magnetic body 41 loses a polarity temporarily, but has a polarity again by the magnetic force generated by the second coil 32.

In this case, since the moving magnetic body 41 is affected by the magnetic force by the second coil 32, the moving magnetic body 41 has the same polarity as that of the stationary magnetic body 61.

Electrical attraction between the stationary magnetic body 61 and the moving magnetic body 41 is generated so that the stationary magnetic body 61 pulls the moving magnetic body 41. Since the stationary magnetic body 61 is fixedly installed, the stationary magnetic body 61 does not move.

Thus, the piston 40 moves backward by force pulled by the stationary magnetic body 61.

Referring to FIG. 5B, when the piston 40 moves backward, pressure in the drug accommodating portion 22 is lowered and thus, the nozzle portion opening/closing valve 50 is elastically restored and is closed.

In addition, when the pressure in the drug accommodating portion 22 is lowered, the drug may be filled in the drug accommodating portion 22 from the drug filling device 25 through the drug supply hole 22*c*. That is, when the piston 40 moves backward, the drug may be automatically filled.

Meanwhile, the current supply unit supplies a current to the second coil 32 for a second preset time and then, when the second preset time elapses, the current supply unit cuts off the current.

Referring to FIG. 4B, a case where the second preset time is about 20 ms, will be described.

Since current is applied to the second coil 32 to move the piston 40 backward, the magnetic force generated by the second coil 32 is set smaller than the magnetic force generated by the first coil 31. Thus, since a weaker magnetic force is generated around the second coil 32, the time during which a current is applied to move the piston 40 backward is set longer than the time during which a current is applied to the first coil 31. In addition, the time applied to the second coil 32 may be increased or decreased according to the number of repeated injections per second of the drug. For example, when the number of repeated injections per second is increased to 50 to 100 Hz or more, the time applied to the second coil 32 may be set shorter.

When the second preset time elapses, the current supply unit cuts off the supply of current to the second coil 32 and supplies current to the first coil 31 so that the piston 40 may be moved forward again.

As described above, current is selectively supplied or cut off to one of the first coil 31 and the second coil 32 so that the forward movement and the backward movement of the piston 40 can be repeated.

Thus, because a small amount of the drug can be repeatedly injected at high speed, a small amount of the drug can be injected into the entire skin several times in the field of skin care and the like.

Meanwhile, FIG. 6 is a cross-sectional view showing a needleless syringe according to a second embodiment of the present invention.

Referring to FIG. 6, a needleless syringe 200 according to the second embodiment of the present invention is different from that of the first embodiment in that the needleless syringe 200 according to the second embodiment of the present invention further includes a cooling chamber 210 for cooling heat generated in the solenoid coil 30 through a cooling fluid, and the rest of the configuration and operation thereof is similar to those of the first embodiment, and thus, a description of the similar configurations will be omitted, and different configurations will be mainly described below.

The cooling chamber 210 is detachably coupled to the outside of the body 10.

The cooling chamber 210 includes a first cooling chamber 211 installed to surround the first coil 31 on the outer circumferential surface of the body 10, and a second cooling chamber 212 installed to surround the second coil 32 on the outer circumferential surface of the body 10.

A first cooling fluid supply pipe 211*a* and a first cooling fluid discharge pipe 211*b* are coupled to the first cooling chamber 211.

The first cooling fluid supply pipe 211*a* is a flow path for supplying a cooling fluid from the outside to the first cooling chamber 211.

The first cooling fluid discharge pipe 211*b* is a flow path for discharging the cooling fluid of the first cooling chamber 211 to the outside.

An opening/closing valve (not shown) may be provided in the first cooling fluid supply pipe 211*a* and the first cooling fluid discharge pipe 211*b*, respectively.

A second cooling fluid supply pipe 212*a* and a second cooling fluid discharge pipe 212*b* are coupled to the second cooling chamber 212.

The second cooling fluid supply pipe 212*a* is a flow path for supplying the cooling fluid from the outside to the second cooling chamber 212.

The second cooling fluid discharge pipe 212*b* is a flow path for discharging the cooling fluid of the second cooling chamber 212 to the outside.

An opening/closing valve (not shown) may be provided in the second cooling fluid supply pipe 212*a* and the second cooling fluid discharge pipe 212*b*, respectively.

In the present embodiment, a case where two cooling chambers 210 are provided, has been described, but the present invention is not limited thereto, and of course, one cooling chamber 210 may also be provided to surround both the first coil 31 and the second coil 32.

In addition, in the present embodiment, a cooling fluid is used to cool the solenoid coil 30, and water or air is used as the cooling fluid. However, the present invention is not limited, and a conduction cooling method or the like may be used.

The needleless syringe 200 according to the second embodiment of the present invention configured as described above is provided with the cooling chamber 210 for cooling the solenoid coil 30, so that heat of the solenoid coil 30 can be absorbed and the solenoid coil can be kept at a constant temperature and thus, the magnetic force can be prevented from being weakened by the heat generated by the solenoid coil 30.

Meanwhile, FIG. 7 is a view showing a forward movement state of a piston of a needleless syringe according to a third embodiment of the present invention.

FIG. 8 is a view showing a backward movement state of the piston of the needleless syringe according to the third embodiment of the present invention.

Referring to FIGS. 7 and 8, a needleless syringe 300 according to the third embodiment of the present invention is different from those of the first and second embodiments in that the needleless syringe 300 further includes a recoil offset part 310 for offsetting recoil generated during the forward movement or the backward movement of the piston 40, and the reset of configurations and operations are similar to those of the above embodiments, and thus only different configurations will be described.

The recoil offset part 310 is provided to be symmetrical with the moving magnetic body 41 around the stationary magnetic body 32.

The recoil offset part 310 includes a coil 311 for recoil offsetting, a moving magnetic body 312 for recoil offsetting, and a current supply unit (not shown) for recoil offsetting.

The coil 311 for recoil offsetting is wound on the outer circumferential surface of the body 10 at a position where it is spaced apart from the solenoid valve 30 backward by a certain distance. A case where the length of the coil 311 for recoil offsetting is the same as the length of the first coil 31, will be described.

The moving magnetic body 312 for recoil offsetting is a magnetic body inserted into the body 10 to be spaced apart from the piston 40 backward by a certain distance. The moving magnetic body 312 for recoil offsetting is provided to be symmetrical with the moving magnetic body 41 around the stationary magnetic body 32.

The moving magnetic body 321 for recoil offsetting may include one of a ferromagnet, a quasi ferromagnet, and a permanent magnet, or a combination of two or more thereof.

In the present embodiment, the moving magnetic body 312 for recoil offsetting will be described as having the same size and material as the moving magnetic body 41.

The current supply unit (not shown) for recoil offsetting supplies current in a different direction from a direction of current applied to the first coil 31 to the coil for recoil offsetting 311 so that the direction of the magnetic force generated by the first coil 31 and the direction of the magnetic force generated by the coil 311 for recoil offsetting may be opposite to each other.

The operation of the needleless syringe 300 according to the third embodiment of the present invention having the above configuration will be described as follows.

Referring to FIG. 7, when the piston 40 moves forward, current is applied to the first coil 31, and the supply of current to the second coil 32 is cut off, and current in an opposite direction to the direction of current applied to the first coil 31 is applied to the coil 311 for recoil offsetting.

That is, currents are simultaneously supplied to the first coil 31 and the coil 311 for recoil offsetting, wherein the currents are supplied in opposite directions.

The magnetic force generated by the first coil 31 causes the piston 40 to move forward.

The magnetic force generated by the coil 311 for recoil offsetting 311 causes the moving magnetic body 312 for recoil offsetting to move backward.

That is, the piston 40 and the moving magnetic body 312 for recoil offsetting move in opposite directions.

Thus, when the piston 40 moves forward, recoil generated in the needleless syringe 300 backward may be offset by recoil generated in the needleless syringe 300 forward when the moving magnetic body 312 for recoil offsetting moves backward.

In addition, referring to FIG. 8, when the piston 40 moves backward, the supply of current to the first coil 31 is cut off, and current is supplied to the second coil 32, and current in an opposite direction to the direction of current applied to the second coil 31 is applied to the coil 311 for recoil offsetting.

When a current is supplied to the second coil 31, a magnetic force between the second coil 32 and the stationary magnetic body 61 is generated.

When the supply of current to the first coil 31 is cut off, the magnetic force generated by the first coil 31 disappears and thus, the moving magnetic body 41 loses a polarity temporarily, but has a polarity again by the magnetic force generated by the second coil 32.

In this case, the moving magnetic body 41 is affected by the magnetic force by the second coil 31 and thus has the same polarity as that of the stationary magnetic body 61.

Electrical attraction between the stationary magnetic body 61 and the moving magnetic body 41 is generated so that the stationary magnetic body 61 pulls the moving magnetic body 41. The stationary magnetic body 61 is fixedly installed and thus does not move.

Thus, the piston 40 moves backward by force pulled by the stationary magnetic body 61.

Meanwhile, the magnetic force generated by the coil 311 for recoil offsetting causes the moving magnetic body 312 for recoil offsetting to move forward.

That is, the piston 40 and the moving magnetic body 312 for recoil offsetting move in opposite directions.

Thus, when the piston 40 moves backward, recoil generated in the needleless syringe 300 forward may be offset by recoil generated in the needleless syringe 300 backward when the moving magnetic body 312 for recoil offsetting moves forward.

Since recoil generated whenever the piston 40 reciprocates forward/backward may be offset by using the above-described method, discomfort caused by recoil felt by the user when using the needleless syringe 300 can be eliminated.

In the present embodiment, a case where the solenoid coil 30 includes two first and second coils 31 and 32, has been described, but the present invention is not limited thereto, and of course, the solenoid coil 30 may include only the first coil 31, and only the supply direction of current may be changed.

Meanwhile, FIG. 9 is a view showing a forward movement state of a piston of a needleless syringe according to a fourth embodiment of the present invention. FIG. 10 is a view showing a backward movement state of the piston of the needleless syringe according to the fourth embodiment of the present invention.

Referring to FIGS. 9 and 10, a needleless syringe 400 according to a fourth embodiment of the present invention is different from the first embodiment in that the solenoid coil 30 includes two first and second coils 31 and 32 and an inner circumferential surface of the body 10 in which the second coil 32 is wound, is formed of an empty space S in which a separate magnetic body is not inserted, and the rest of the configuration and operation thereof is similar to those of the first embodiment, and thus, a description of the similar configurations will be omitted, and different configurations will be mainly described below.

Referring to FIG. 9, when the piston 40 moves forward, the forward/backward driving unit applies current to the first coil 31 and cuts off the supply of current to the second coil 32.

When a current is applied to the first coil 31, a magnetic force generated by the first coil 31 causes the piston 40 to move forward.

When the piston 40 moves forward, the pressurizing portion 42 pressurizes the drug in the drug accommodating portion 22, and the nozzle portion opening/closing valve 50 is opened by the hydraulic pressure of the drug. When the nozzle portion opening/closing valve 50 is opened, the drug in the drug accommodating portion 22 may be sprayed forward through the nozzle portion 23.

Referring to FIG. 10, when the piston 40 moves backward, the forward/backward driving unit cuts off the supply of current to the first coil 31 and supplies current to the second coil 32.

When a current is supplied to the second coil 32, a magnetic force is generated in the space S. The inside of the space S is polarized.

In addition, when the supply of current to the first coil 31 is cut off, the magnetic force generated by the first coil 31 disappears and thus the moving magnetic body 41 loses a polarity temporarily, but has a polarity again by the magnetic force generated by the second coil 32.

In this case, the moving magnetic body 41 is affected by the magnetic force caused by the second coil 31 and thus has the same polarity as that of the space S.

The moving magnetic body 41 moves backward by the magnetic force generated in the space S.

Thus, the piston 40 moves backward.

The current supply unit repeatedly supplies current to the first coil 31 and the second coil 32 alternately or cuts off the supply of current so that the piston 40 may be moved forward or backward.

Meanwhile, FIG. 11 is a view showing a forward movement state of a piston of a needleless syringe according to a fifth embodiment of the present invention. FIG. 12 is a view showing a backward movement state of the piston of the needleless syringe according to the fifth embodiment of the present invention.

Referring to FIGS. 11 and 12, a needleless syringe 500 according to the fifth embodiment of the present invention is different from the above-described embodiments in that the needleless syringe 500 includes only one solenoid coil 30 and a forward/backward driving unit that repeats the forward movement and the backward movement of the piston 40 includes a current supply unit (not shown) for moving the piston 40 forward by repeating the supply and cut off of current to the solenoid coil 40 at a preset period and an elastic member for applying an elastic force in a direction in which the piston 40 moves backward, when the supply of current of the current supply unit (not shown) is cut off, and the rest of the configuration and operation thereof is similar to those of the first embodiment, and thus, a description of the similar configurations will be omitted, and different configurations will be mainly described below.

The elastic member includes a first elastic member 510 installed between the body 10 and the moving magnetic body 41 of the piston 40, and a second elastic member 520 installed between the cylinder 20 and the pressurizing portion 42 of the piston 40.

The first elastic member 510 is a spring that is compressed when the moving magnetic body 41 moves forward by a current supplied to the solenoid coil 30 and applies an elastic force to the moving magnetic body 41 in the backward movement direction of the moving magnetic body 41 when the supply of current to the solenoid coil 30 is cut off.

The second elastic member 520 is a spring that is compressed when the pressurizing portion 42 moves forward by a current supplied to the solenoid coil 30 and applies an elastic force to the pressurizing portion 42 in the backward movement direction of the pressurizing portion 42 when the supply of current to the solenoid coil 30 is cut off.

FIG. 13 is a graph showing an example of a current supply waveform applied to a solenoid coil of the needleless syringe according to the fifth embodiment of the present invention.

Referring to FIG. 13, the current supply unit (not shown) applies a voltage of about 100 V to the solenoid coil 30 for 10 to 50 ms when the piston 40 moves forward and cuts off the voltage to the solenoid coil 30 when the piston 40 moves backward. A case where time at which the supply of voltage to the solenoid coil 30 is cut off, is set to be the same as time at which voltage is applied to the solenoid coil 30, will be described.

The magnitude of time or voltage applied to the solenoid coil 30 may be variously set in consideration of the amount of the drug or the like.

Meanwhile, FIG. 14 is a graph showing another example of a current supply waveform applied to the solenoid coil of the needleless syringe according to the fifth embodiment of the present invention.

Referring to FIG. 14, the current supply unit (not shown) may change the direction of current applied to the solenoid coil 30 repeatedly at a preset period to change the direction of a magnetic force generated in the solenoid coil 30 periodically.

A case where the current supply unit (not shown) applies voltage of about 100 V to the solenoid coil 30 when the piston 40 moves forward and applies voltage of about ??100 V to the solenoid coil 30 when the piston 40 moves backward, will be described.

Thus, when voltage of 100 V is applied to the solenoid coil 30, a magnetic force is generated in a direction in which the piston 40 moves forward, so that the piston 40 may move forward.

In addition, when voltage of ??100 V is applied to the solenoid coil 30, a magnetic force is generated in a direction in which the piston 40 moves backward, so that the piston 40 may move backward.

In addition, the present invention is not limited thereto, and the current supply unit (not shown) may include a capacitor (not shown) that stores current supplied from an external power supply source, supplies the stored current when the piston 40 moves forward and cuts off the supply of current to the solenoid coil 30 when the piston 40 moves backward, and a DC power supply unit that supplies current supplied from the external power supply source to the solenoid coil 30 when the piston 40 moves backward.

That is, the current supply unit (not shown) may change the direction of current applied to the solenoid coil 30 at a preset period repeatedly, supply current stored in the capacitor (not shown) when the piston 40 moves forward, supply current from the DC power supply unit when the piston 40 moves backward, thereby increasing a moving speed when the piston 40 moves forward.

Meanwhile, FIG. 15 is a cross-sectional view showing a needleless syringe according to a sixth embodiment of the present invention.

Referring to FIG. 15, a needleless syringe 600 according to the sixth embodiment of the present invention is different from the fifth embodiment in that the needleless syringe 600 further includes a cooling chamber 610 for cooling heat generated in the solenoid coil 30 through a cooling fluid, and the rest of the configuration and operation thereof is similar to those of the first embodiment, and thus, a description of the similar configurations will be omitted, and different configurations will be mainly described below.

The cooling chamber 610 is detachably coupled to the outside of the body 10.

The cooling chamber 610 is installed to surround the solenoid coil 30 on the outer circumferential surface of the body 10. A cooling fluid supply pipe 611 and a cooling fluid discharge pipe 612 are coupled to the cooling chamber 610.

The cooling fluid supply pipe 611 is a flow path for supplying a cooling fluid from the outside to the cooling chamber 610. The cooling fluid discharge pipe 612 is a flow path for discharging the cooling fluid of the cooling chamber 610 to the outside. An opening/closing valve (not shown) may be provided in the cooling fluid supply pipe 611 and the cooling fluid discharge pipe 612, respectively.

In addition, in the present embodiment, a case where a cooling fluid is used to cool the solenoid coil 30 and water or air is used as the cooling fluid, will be described, but the present invention is not limited thereto, and a conduction cooling method or the like may also be used.

The needleless syringe 600 according to the sixth embodiment of the present invention configured as described above is provided with the cooling chamber 610 for cooling the solenoid coil 30, so that heat of the solenoid coil 30 can be absorbed and the solenoid coil can be kept at a constant temperature and thus, the magnetic force can be prevented from being weakened by the heat generated by the solenoid coil 30.

Meanwhile, FIG. 17 is a view showing a backward movement state of the piston of the needleless syringe according to the seventh embodiment of the present invention, and FIG. 18 is a cross-sectional view showing a needleless syringe according to an eighth embodiment of the present invention.

Referring to FIGS. 17 and 18, a needleless syringe 700 according to the seventh embodiment of the present invention is different from the fifth embodiment in that the needleless syringe 700 according to the seventh embodiment of the present invention further includes one solenoid coil 30 and further includes a recoil offset part 710 for offsetting recoil generated when the piston 40 moves forward or backward, and the rest of the configuration and operation thereof is similar to those of the fifth embodiment, and thus, a description of the similar configurations will be omitted, and different configurations will be mainly described below.

The recoil offset part 710 includes a coil 711 for recoil offsetting, a moving magnetic body 712 for recoil offsetting, and a current supply unit (not shown) for recoil offsetting.

The coil 711 for recoil offsetting is wound on the outer circumferential surface of the body 10 in a position in which the coil 711 for recoil offsetting is spaced apart from the solenoid coil 30 backward. A case where the length of the coil 711 for recoil offsetting is the same as the length of the solenoid coil 30, will be described.

The moving magnetic body 712 for recoil offsetting is a magnetic body inserted into the body 10 to be spaced apart from the piston 40 backward by a certain distance. The moving magnetic body 712 for recoil offsetting may be formed to correspond the size of the moving magnetic body 41 of the piston 40.

The moving magnetic body 712 for recoil offsetting may include one of a ferromagnet, a quasi ferromagnet, and a permanent magnet, or a combination of two or more thereof.

In the present embodiment, a case where the size and material of the moving magnetic body 712 for recoil offsetting are the same as those of the moving magnetic body 41, will be described.

The current supply unit (not shown) for recoil offsetting supplies current in a different direction from a direction of current applied to the solenoid coil 30 to the coil 711 for recoil offsetting so that the direction of a magnetic force generated by the solenoid coil 30 and the direction of a magnetic force generated by the coil 711 for recoil offsetting are opposite to each other.

The operation of the needleless syringe 700 according to the seventh embodiment of the present invention having the above configuration will be described as follows.

Referring to FIG. 17, when the piston 40 moves forward, current is applied to the solenoid coil 30, and current in an opposite direction to the direction of current applied to the solenoid coil 30 is applied to the coil 711 for recoil offsetting.

That is, currents are simultaneously supplied to the solenoid coil 30 and the coil 711 for recoil offsetting, wherein the currents are supplied in opposite directions.

The magnetic force generated by the solenoid coil 30 causes the piston 40 to move forward.

The magnetic force generated by the coil 611 for recoil offsetting causes the moving magnetic body 712 for recoil offsetting to move backward.

That is, the piston 40 and the moving magnetic body 712 for recoil offsetting move in opposite directions.

Thus, recoil generated in the needleless syringe 700 backward when the piston 40 moves forward may be offset by recoil generated forward when the moving magnetic body 712 for recoil offsetting moves backward.

In addition, referring to FIG. 18, when the piston 40 moves backward, the supply of current to the solenoid coil 30 is cut off, and current in an opposite direction to the direction of current applied to the solenoid coil 30 is applied to the coil 711 for recoil offsetting.

The magnetic force generated by the solenoid coil 30 causes the piston 40 to move backward.

The magnetic force generated by the coil 711 for recoil offsetting causes the moving magnetic body 712 for recoil offsetting to move forward.

That is, the piston 40 and the moving magnetic body 712 for recoil offsetting move in opposite directions.

Thus, recoil generated in the needleless syringe 700 forward when the piston 40 moves backward may be offset by recoil generated in the needleless syringe 700 backward when the moving magnetic body 712 for recoil offsetting moves forward.

Since recoil generated whenever the piston 40 reciprocates forward/backward may be offset by using the above-described method, discomfort caused by recoil felt by the user when using the needleless syringe 700 can be eliminated.

Meanwhile, FIG. 18 is a cross-sectional view showing a needleless syringe according to an eighth embodiment of the present invention.

Referring to FIG. 18, a needleless syringe 800 according to the eighth embodiment of the present invention is different from that of the above embodiments in that the needleless syringe 800 according to the eighth embodiment of the present invention includes a piston cover 810 between the cylinder 20 and the piston 40, and the rest of the configuration and operation thereof is similar to those of the above embodiments, and thus, a description of the similar configurations will be omitted, and different configurations will be mainly described below.

The piston cover 810 is fixedly installed on the cylinder 20. The piston cover 810 is provided inside the cylinder 20 and is disposed to cover the end portion of the piston 40. The piston cover 810 may be inserted and coupled to the inside of the cylinder 20, and may be fixed to the inner circumferential surface of the cylinder 20 by bonding or coupling.

The piston cover 810 is formed of a stretchable material so as to be stretched forward by the piston 40 when the piston 40 moves forward and to be restored when the piston 40 moves backward. In the present embodiment, the piston cover 810 will be described as an example of a rubber diaphragm.

The piston cover 810 may prevent the drug from directly staining the end portion of the piston 40.

Thus, there is no need for the user to wipe the end portion of the piston 40.

In addition, because the piston cover 810 is provided in the cylinder 20, the piston cover 810 is also replaceable when the cylinder 20 is replaced.

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

According to the present invention, a needleless syringe in which multiple injections, rather than a single injection, are possible during a single procedure to a wider range of skin such as that of the face in the fields of skin care and the like, can be manufactured.

The invention claimed is:

1. A needleless syringe comprising:

a body;

a solenoid coil wound on an outer circumferential surface of the body;

a cylinder coupled to the body to be in communication with an open front surface of the body and comprising a drug accommodating portion in which the drug is accommodated, and a nozzle portion injecting the drug accommodated in the drug accommodating portion forward;

a piston comprising a moving magnetic body that is inserted into the body in a longitudinal direction and reciprocates forward and backward by a magnetic force generated when a current is applied to the solenoid coil, and a pressurizing portion that extends from the moving magnetic body, is inserted into the cylinder in the longitudinal direction and presses the drug in the drug accommodating portion to the nozzle portion in conjunction with the forward and backward reciprocating motion of the moving magnetic body, the moving magnetic body and the pressurizing portion being integrally formed with each other;

a nozzle portion opening/closing valve that is provided to open/close a passage hole between the nozzle portion and the drug accommodating portion; and a forward/backward driving unit that repeats a supply and cut-off of current to the solenoid coil at a preset period, thereby repeating the forward movement and the backward movement of the piston, wherein the solenoid coil comprises:

a first coil, which is wound on front of the outer circumferential surface of the body, to which a current is applied during forward movement of the piston and generates a magnetic force in a forward movement direction of the piston; and a second coil, which is wound on rear of the first coil on the outer circumferential surface of the body, to which a current is applied during backward movement of the piston and generates a magnetic force to cause the piston to move backward, and the forward/backward driving unit comprises:

a stationary magnetic body that is inserted at a position where the stationary magnetic body is spaced apart from the moving magnetic body backward from the inside of the body and is fixed, is magnetized by a magnetic force generated when a current is applied to the second coil, and pulls the moving magnetic body in a backward movement direction due to electrical attraction; and a current supply unit that repeatedly supplies a current to the first coil and cuts off supply of current to the second coil during forward movement of the piston and repeatedly cuts off supply of current to the first coil and supplies a current to the second coil during backward movement of the piston.

2. The needleless syringe of claim 1, further comprising a cooling chamber that is provided to surround an outside of the solenoid coil on an outside of the body and absorbs and cools heat generated in the solenoid coil through a cooling fluid.

3. The needleless syringe of claim 1, further comprising a recoil offset part offsetting recoil generated when the piston moves forward or backward, wherein the recoil offset part comprises:

a coil for recoil offsetting that is wound on the outer circumferential surface of the body in a position in which the coil for recoil offsetting is spaced apart from the solenoid coil backward;

a moving magnetic body for recoil offsetting that is inserted into the body to be spaced apart from the piston backward by a certain distance and is provided to reciprocate forward/backward in an opposite direction to a direction of the piston due to a magnetic force generated when a current is applied to the coil for recoil offsetting; and a current supply unit for recoil offsetting that, when a current is supplied to the solenoid coil, supplies current in an opposite direction to a direction of current applied to the solenoid coil to the coil for recoil offsetting so as to generate a magnetic force in an opposite direction to a movement direction of the piston.

4. The needleless syringe of claim 1, further comprising a flange portion that protrudes in a radial direction and is formed on an outer circumferential surface of the pressurizing portion and a blocker that is provided between the pressurizing portion and the cylinder and limits a forward movement distance of the piston due to the flange portion blocked when the piston moves forward, wherein the blocker comprises:

a length adjustment blocker that adjusts a length at which the length adjustment blocker protrudes backward.

5. The needleless syringe of claim 1, wherein a drug supply hole for supplying the drug from the outside by a pressure difference generated when the piston moves backward, is formed in the drug accommodating portion.

6. The needleless syringe of claim 5, wherein the nozzle portion opening/closing valve opens the passage hole with a fluidic pressure applied by the drug from the drug accommodating portion when the piston moves forward, and closes the passage hole when the fluidic pressure is released.

7. The needleless syringe of claim 1, wherein the moving magnetic body is formed of one of a ferromagnet, a quasi-ferromagnet, and a permanent magnet, or a combination of two or more of the ferromagnet, the quasi-ferromagnet, and the permanent magnet.

8. The needleless syringe of claim 1, wherein the stationary magnetic body is formed of one of a ferromagnet, a quasi-ferromagnet, and a permanent magnet, or a combination of two or more of the ferromagnet, the quasi-ferromagnet, and the permanent magnet.

9. The needleless syringe of claim 1, wherein the current supply unit supplies the current supplied from an external power supply source to the first coil and the second coil.

10. The needleless syringe of claim 1, further comprising a piston cover that is provided inside the cylinder to cover an end portion of the piston.

11. The needleless syringe of claim 1, wherein the forward/backward driving unit further comprises an elastic member that is installed between the piston and the cylinder and applies an elastic force to the piston in a backward movement direction when the piston moves backward.

12. A needleless syringe comprising:

a body;

a solenoid coil wound on an outer circumferential surface of the body;

a cylinder coupled to the body to be in communication with an open front surface of the body and comprising a drug accommodating portion in which the drug is accommodated, and a nozzle portion injecting the drug accommodated in the drug accommodating portion forward;

a piston comprising a moving magnetic body that is inserted into the body in a longitudinal direction and reciprocates forward and backward by a magnetic force generated when a current is applied to the solenoid coil, and a pressurizing portion that extends from the moving magnetic body, is inserted into the cylinder in the longitudinal direction and presses the drug in the drug accommodating portion to the nozzle portion in conjunction with the forward and backward reciprocating motion of the moving magnetic body;

a nozzle portion opening/closing valve that is provided to open/close a passage hole between the nozzle portion and the drug accommodating portion; and a forward/backward driving unit that repeats a supply and cut-off of current to the solenoid coil at a preset period, thereby repeating the forward movement and the backward movement of the piston, wherein the solenoid coil comprises:

a first coil, which is wound on front of the outer circumferential surface of the body, to which a current is applied during forward movement of the piston and generates a magnetic force in a forward movement direction of the piston; and a second coil, which is wound on rear of the first coil on the outer circumferential surface of the body, to which a current is applied during backward movement of the piston and generates a magnetic force to cause the piston to move backward, and the forward/backward driving unit comprises:

a stationary magnetic body that is inserted at a position where the stationary magnetic body is spaced apart from the moving magnetic body backward from the inside of the body and is fixed, is magnetized by a magnetic force generated when a current is applied to the second coil, and pulls the moving magnetic body in a backward movement direction due to electrical attraction; and a current supply unit that repeatedly supplies a current to the first coil and cuts off supply of current to the second coil during forward movement of the piston and repeatedly cuts off supply of current to the first coil and supplies a current to the second coil during backward movement of the piston, the needleless syringe further comprising:

a recoil offset part offsetting recoil generated when the piston moves forward or backward;

a flange portion that protrudes in a radial direction and is formed on an outer circumferential surface of the piston; and a blocker that is provided between the piston and the cylinder and limits a forward movement distance of the piston due to the flange portion blocked when the piston moves forward.

13. A needleless syringe comprising:

a body;

a solenoid coil wound on an outer circumferential surface of the body;

a cylinder coupled to the body to be in communication with an open front surface of the body and comprising a drug accommodating portion in which the drug is accommodated, and a nozzle portion injecting the drug accommodated in the drug accommodating portion forward;

a piston comprising a moving magnetic body that is inserted into the body in a longitudinal direction and reciprocates forward and backward by a magnetic force generated when a current is applied to the solenoid coil, and a pressurizing portion that extends from the moving magnetic body, is inserted into the cylinder in the longitudinal direction and presses the drug in the drug accommodating portion to the nozzle portion in conjunction with the forward and backward reciprocating motion of the moving magnetic body;

a nozzle portion opening/closing valve that is provided to open/close a passage hole between the nozzle portion and the drug accommodating portion;

a forward/backward driving unit that repeats a supply and cut-off of current to the solenoid coil at a preset period, thereby repeating the forward movement and the backward movement of the piston; and a piston cover that is provided inside the cylinder in front of the piston to cover an end portion of the piston and is formed of a stretchable material so as to be stretched forward by the piston when the piston moves forward, wherein the cylinder comprises a first block and a second block, the first block including a cylinder main hole and the drug accommodating portion, the second block including the nozzle portion, and the first block and the second block being coupled to each other.

14. The needleless syringe of claim 13, wherein the solenoid coil comprises:

a first coil, which is wound on front of the outer circumferential surface of the body, to which a current is applied during forward movement of the piston and generates a magnetic force in a forward movement direction of the piston; and a second coil, which is wound on rear of the first coil on the outer circumferential surface of the body, to which a current is applied during backward movement of the piston and generates a magnetic force to cause the piston to move backward.

15. The needleless syringe of claim 14, wherein the forward/backward driving unit comprises:

a current supply unit that repeatedly supplies a current to the first coil and cuts off supply of current to the second coil during forward movement of the piston and repeatedly cuts off supply of current to the first coil and supplies a current to the second coil during backward movement of the piston; and an elastic member that is installed between the piston and the cylinder and applies an elastic force to the piston in a backward movement direction when the moving magnetic body moves backward.

16. The needleless syringe of claim 13, wherein the forward/backward driving unit comprises:

a current supply unit that repeatedly supplies a current to the solenoid coil and cuts off supply of current to the solenoid coil at a preset period to move the piston forward;

a first elastic member that is installed between the body and the piston and applies an elastic force in a backward movement direction of the piston when supply of current of the current supply unit is cut off; and a second elastic member that is installed between the cylinder and the piston and applies an elastic force in a backward movement direction of the piston when supply of current of the current supply unit is cut off.

17. The needleless syringe of claim 13, wherein the forward/backward driving unit comprises a current supply unit that changes a direction of current applied to the solenoid coil at a preset period repeatedly to change a direction of a magnetic force generated when a current is applied to the solenoid coil periodically, to repeat forward movement and backward movement of the piston periodically.

18. The needleless syringe of claim 17, wherein the current supply unit supplies a current supplied from an external power supply source to the solenoid coil.

19. The needleless syringe of claim 13, further comprising a cooling chamber that is provided to surround an outside of the solenoid coil on an outside of the body and absorbs and cools heat generated in the solenoid coil through a cooling fluid.

20. The needleless syringe of claim 13, further comprising a recoil offset part offsetting recoil generated when the piston moves forward or backward, wherein the recoil offset part comprises:

a coil for recoil offsetting that is wound on the outer circumferential surface of the body in a position in which the coil for recoil offsetting is spaced apart from the solenoid coil backward;

a moving magnetic body for recoil offsetting that is inserted into the body to be spaced apart from the piston backward by a certain distance and is provided to reciprocate forward/backward in an opposite direction to a direction of the piston due to a magnetic force generated when a current is applied to the coil for recoil offsetting; and a current supply unit for recoil offsetting that, when a current is supplied to the solenoid coil, supplies current in an opposite direction to a direction of current applied to the solenoid coil to the coil for recoil offsetting so as to generate a magnetic force in an opposite direction to a movement direction of the piston.

* * * * *